United States Patent
Chauhan et al.

(10) Patent No.: US 11,806,382 B2
(45) Date of Patent: Nov. 7, 2023

(54) METHODS OF INHIBITING INTEGRIN α9β1 ACTIVITY

(71) Applicant: UNIVERSITY OF IOWA RESEARCH FOUNDATION, Iowa City, IA (US)

(72) Inventors: Anil K. Chauhan, Iowa City, IA (US); Nirav A. Dhanesha, Iowa City, IA (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 0 days.

(21) Appl. No.: 16/951,650

(22) Filed: Nov. 18, 2020

(65) Prior Publication Data

US 2021/0147556 A1 May 20, 2021

Related U.S. Application Data

(60) Provisional application No. 62/937,021, filed on Nov. 18, 2019.

(51) Int. Cl.

| | |
|---|---|
| *A61K 38/10* | (2006.01) |
| *A61K 38/39* | (2006.01) |
| *A61P 9/10* | (2006.01) |
| *A61K 38/18* | (2006.01) |
| *A61K 38/17* | (2006.01) |
| *A61K 38/19* | (2006.01) |
| *A61K 39/395* | (2006.01) |
| *A61P 29/00* | (2006.01) |
| *C07K 16/28* | (2006.01) |
| *A61K 39/00* | (2006.01) |
| *A61K 9/00* | (2006.01) |
| *C07K 14/47* | (2006.01) |
| *C07K 7/08* | (2006.01) |
| *C07K 14/78* | (2006.01) |
| *C07K 14/46* | (2006.01) |
| *C07K 14/705* | (2006.01) |
| *C07K 14/52* | (2006.01) |

(52) U.S. Cl.
CPC .......... *A61K 38/10* (2013.01); *A61K 38/1703* (2013.01); *A61K 38/1709* (2013.01); *A61K 38/1774* (2013.01); *A61K 38/1866* (2013.01); *A61K 38/19* (2013.01); *A61K 38/39* (2013.01); *A61K 39/3955* (2013.01); *A61P 9/10* (2018.01); *A61P 29/00* (2018.01); *A61K 9/0019* (2013.01); *A61K 2039/505* (2013.01); *A61K 2039/54* (2013.01); *C07K 7/08* (2013.01); *C07K 14/46* (2013.01); *C07K 14/47* (2013.01); *C07K 14/4703* (2013.01); *C07K 14/52* (2013.01); *C07K 14/70503* (2013.01); *C07K 14/78* (2013.01); *C07K 16/2842* (2013.01); *C07K 2317/76* (2013.01)

(58) Field of Classification Search
CPC .......... A61K 38/10; A61K 38/39; A61P 9/10; C07K 7/08; C07K 14/78
See application file for complete search history.

(56) References Cited

U.S. PATENT DOCUMENTS 7,595,045 B2    9/2009   Kurotaki et al.

OTHER PUBLICATIONS

Shinde et al, 2008. Journal of Biological Chemistry. 283(5): 2858-2870.*
Dhanesha et al (2020, Circulation Research. 126: 1779-1794).*
Tokuriki et al, 2009, Current Opinion in Structural Biology. 19: 596-604.*
Bhattacharya et al, 2017. Plos One. 12(3): e0171355, pp. 1-22 as printed.*
Dhanesha, N , et al., "Targeting Myeloid-Specific Integrin α9β1 Improves Short- and Long-Term Stroke Outcomes in Murine Models With Preexisting Comorbidities by Limiting Thrombosis and Inflammation", Cir Res 126 (12), 1779-1794, Supplemental Information, 29 pages (2020).
Dhanesha, N , et al., "Targeting myeloid-cell specific integrin a9b1 inhibits arterial thrombosis in mice", Blood 135 (11), 857-861 (2020).
Dhanesha, N , et al., "Targeting Myeloid-Cell Specific Integrin α9β1 Inhibits Arterial Thrombosis and Improves Stroke Outcome by Limiting Thrombo-inflammation", Session Title: Plenary Session IV: Award Competition, Online Zoom Meeting: Vascular Discovery: From Genes to Medicine, 27 pages (Jun. 29, 2020).

* cited by examiner

*Primary Examiner* — Zachary C Howard
(74) *Attorney, Agent, or Firm* — Viksnins Harris Padys Malen LLP

(57) ABSTRACT

The invention provides a method and kits for inhibiting integrin α9β1 activity comprising contacting integrin α9β1 or a binding partner of integrin α9β1 with an isolated anti-integrin α9 inhibitor, wherein the integrin α9β1 activity is inhibited. In certain aspects, the present invention provides a novel intervention by targeting integrin α9β1 with a functional blocking inhibitor (e.g., peptides or antibodies) to limit brain damage following reperfusion after ischemic stroke.

4 Claims, 17 Drawing Sheets

(9 of 17 Drawing Sheet(s) Filed in Color)

Specification includes a Sequence Listing.

Figures 1A-1G
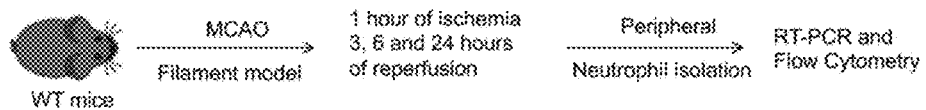
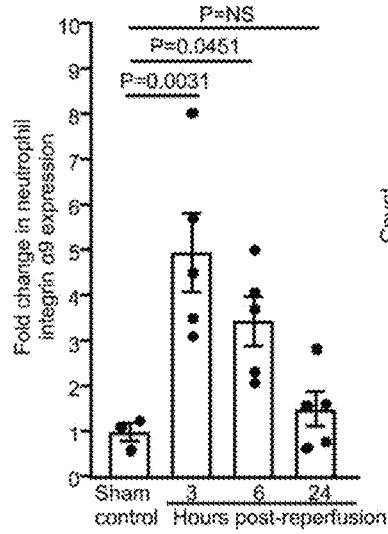
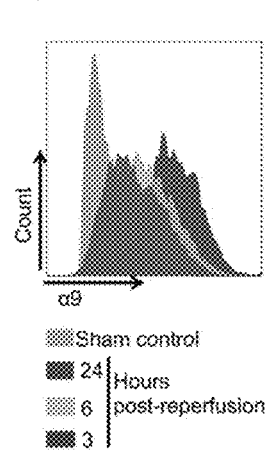
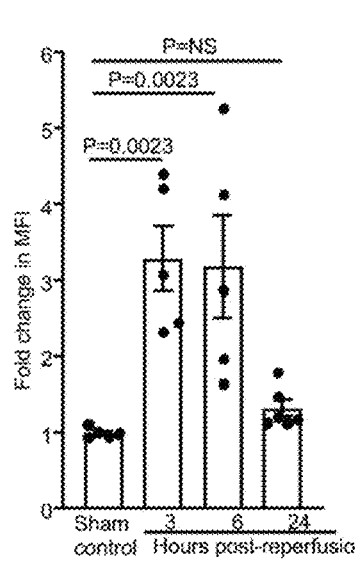
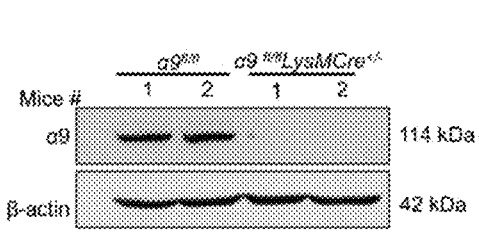
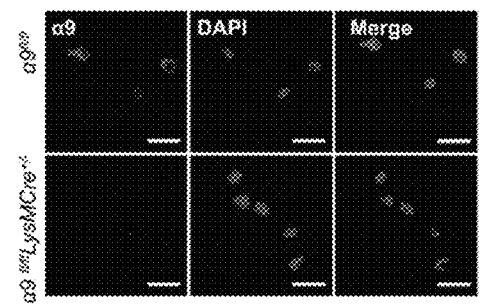
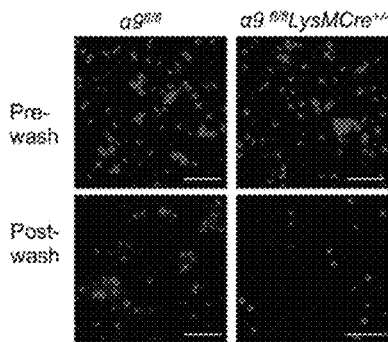
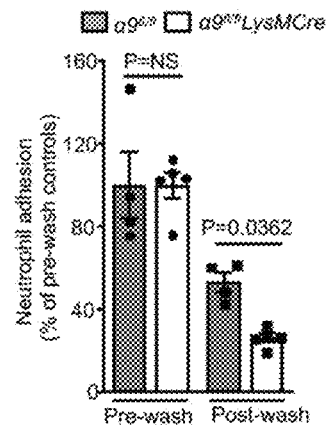
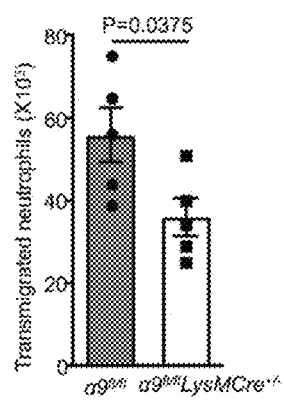

Figures 4G-4H
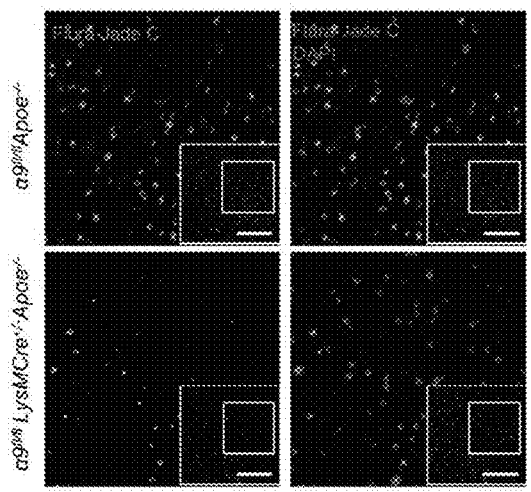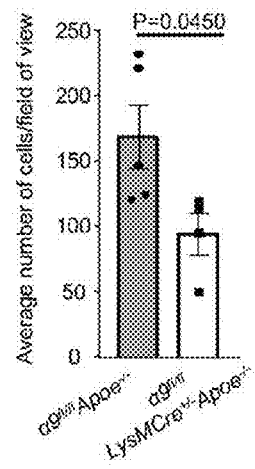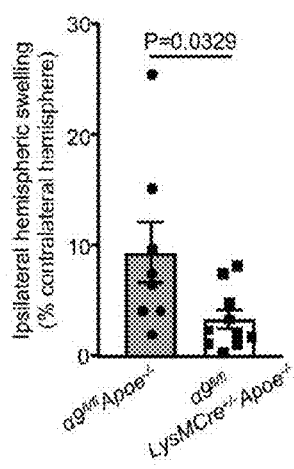

Figures 5A-5E
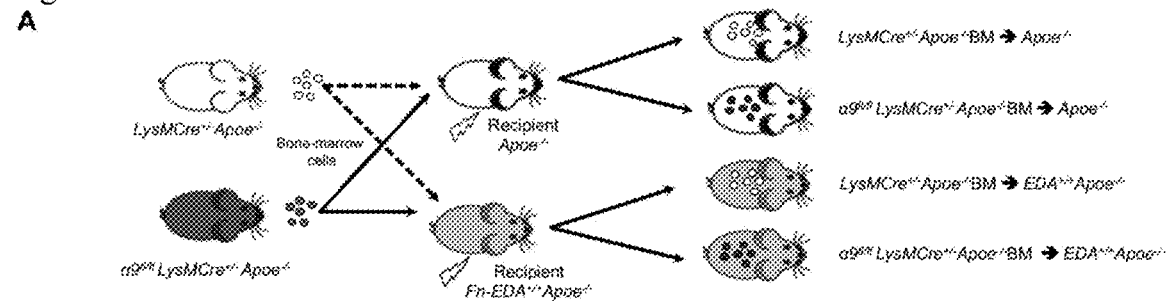
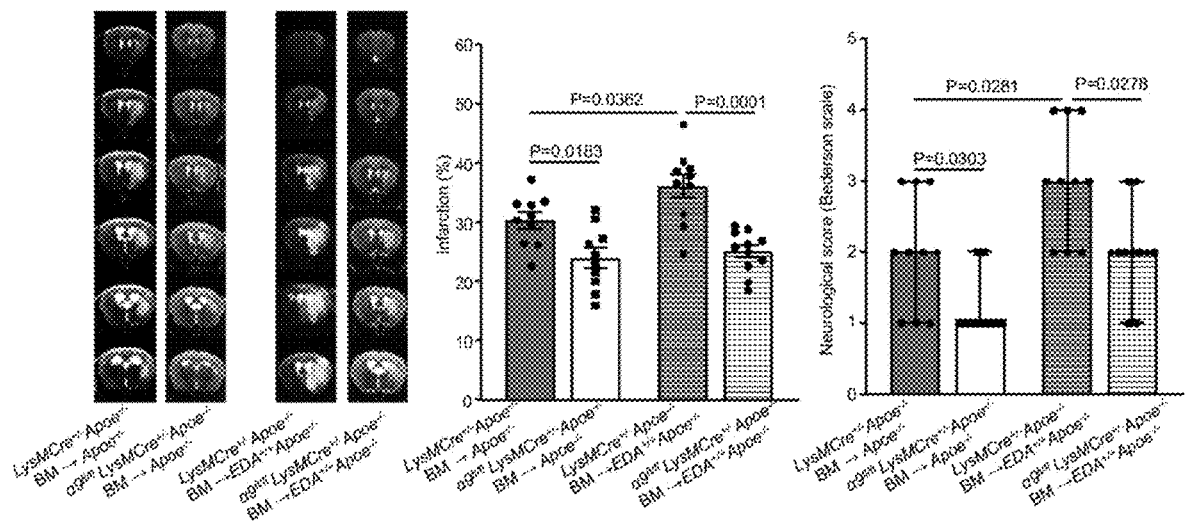
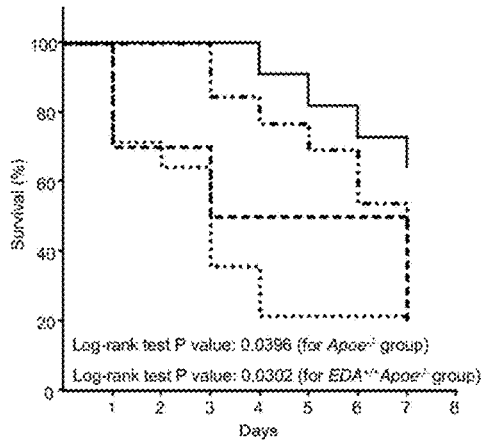
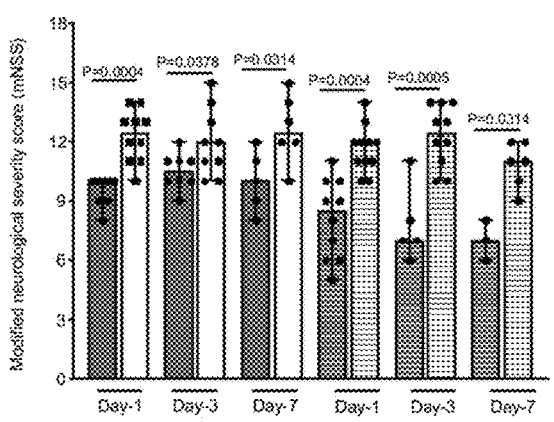

A

METHODS OF INHIBITING INTEGRIN α9β1 ACTIVITY

RELATED APPLICATION

This application claims priority to U.S. Provisional Application No. 62/937,021 that was filed on Nov. 18, 2019. The content of the application referenced above is herein incorporated by reference in its entirety.

STATEMENT REGARDING FEDERALLY SPONSORED RESEARCH

This invention was made with government support under R01NS109910 awarded by National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jun. 2, 2022, is named 17023_232US1_SL.txt and is 2,083 bytes in size.

BACKGROUND OF THE INVENTION

Current treatments for ischemic stroke include thrombolysis using tissue plasminogen activator (tPA) and mechanical thrombectomy. While reperfusion of ischemic brain regions has shown promising clinical outcomes, evidence from clinical studies and animal models suggest that cerebral reperfusion promotes oxidative stress, secondary thrombosis, and vascular inflammation, which aggravate neuronal death in the ischemic penumbra. Antiplatelet agents, including aspirin, P2Y12 antagonists, and glycoprotein IIb/IIIa inhibitors can reduce the risk of secondary thrombosis, but they are associated with increased risk of hemorrhagic transformation. At present, there is no effective intervention available that can efficiently reduce brain damage during reperfusion. A present need exists for novel and effective therapeutic regimens for the treatment of acute ischemic stroke with minimal side-effects. Also, there is a need for effective intervention methods to limit brain damage following reperfusion after ischemic stroke.

SUMMARY OF THE INVENTION

In certain aspects, the present invention provides a method of inhibiting integrin α9β1 activity, comprising contacting integrin α9β1 or a binding partner of integrin α9β1 with an isolated anti-integrin α9 inhibitor, wherein the integrin α9β1 activity is inhibited.

In certain aspects, the present invention provides a method for treating integrin α9β1-related condition in a mammal, comprising administering an effective amount of an isolated anti-integrin α9 inhibitor to the mammal.

In certain aspects, the present invention provides an isolated anti-integrin α9 inhibitor for the prophylactic or therapeutic treatment of an integrin α9β1-related condition.

In certain aspects, the present invention provides a use of an isolated anti-integrin α9 inhibitor to prepare a medicament for the treatment of an integrin α9β1-related condition in a mammal.

In certain aspects, the present invention provides a kit comprising an isolated anti-integrin α9 inhibitor, packaging material, and instructions for administering the inhibitor to a mammal to treat integrin α9β1-related condition.

In certain aspects, the present invention provides a novel intervention by targeting integrin α9β1 with a functional blocking inhibitor (e.g., peptides or antibodies) to limit brain damage following reperfusion after ischemic stroke.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIGS. 1A-1G. Integrin α9-deficient neutrophils exhibit reduced adhesion and trans-endothelial migration. A. Schematic of experimental design. B. Quantification of α9 expression in peripheral neutrophils following ischemia/reperfusion injury by real-time polymerase chain reaction (PCR), n=3, 5, 5 and 5. C. Left: Representative image of flow-cytometric analysis for each group. Right: Quantification of α9 expression in peripheral neutrophils following ischemia/reperfusion injury by flow-cytometry, n=5. D. Western blot analysis of integrin α9 from the bone-marrow-derived neutrophils of the $α9^{fl/fl}$ and $α9^{fl/fl}$ LysMcre$^{+/-}$ mice. E. Representative images showing immunostaining for α9 expression (red) and counterstain by DAPI. Scale bar: 30 µm. Peripheral neutrophils were isolated after 1 hour of ischemia and 3 hours reperfusion and subjected to adhesion assay on TNF (tumor necrosisfactor)-α stimulated brain microvascular endothelial cells. Left: Representative images of calcein-blue labeled neutrophils. Right: Quantification of the adhered neutrophils. n=4, 5, 4, and 5. G. Peripheral neutrophils were isolated after 1 hour of ischemia and 3 hours reperfusion and subjected to trans-migration assay on TNF-α-stimulated brain microvascular endothelial cells, n=5/group. Data represent mean±SEM. Statistical analysis: 1-way ANOVA followed by Holm-Sidak multiple comparisons test (1B, 1C and 1F), unpaired t-test (1G). MCAO indicates middle cerebral artery occlusion.

FIGS. 4A-4H. Deletion of integrin α9 in myeloid cells inhibits post-ischemia/reperfusion inflammation. A. Following one hour ischemia and 23 hours after the reperfusion, perfused ipsilateral hemispheres were homogenized and processed for flow cytometry. Left: show representative dot plots displaying neutrophils in isolated ipsilateral hemispheres from each genotype, and right shows quantification, n=6 and 5. B. Left: Representative dot plots displaying monocytes in isolated ipsilateral hemispheres from each genotype and right panel shows quantification, n=6 and 5. C. Left: Representative immunostained images for neutrophils (brown Ly6B.2-positive cells indicated by red arrows). Boxed region (lower magnification). Inset in the boxed region (higher magnification). Scale bar: 100 Right: Quantification. n=5/group D. Brain homogenates from the infarcted and peri-infarcted area following 1-hour ischemia/ 23 hours reperfusion were processed for Western blotting. Representative Western blots and densitometric analysis of NF-κB p65 (nuclear factor-KB p65). β-Actin was used as a loading control. n=4/group. E and F. Quantification of TNF (tumor necrosis factor)-α and IL (interleukin)-1β levels by ELISA in brain homogenates. n=5/group. G, Representative images for Fluro-jade C (green), and counter-stained with DAPI (stains nuclei, blue). Boxed region (lower magnification). Inset in the boxed region is magnified and shown in the microphotographs. Scale bar: 200 Right: Quantification. Data are mean±SEM, n=5 and 4. H, Ipsilateral edema quantified as extent of edema=(volume of ipsilateral hemisphere−volume of contralateral hemisphere)/volume of contralateral hemisphere×100, n=8 and 10. Data are mean±SEM. Statistical analysis: unpaired t test (A-F and H). MCAO indicates middle cerebral artery occlusion.

FIGS. 5A-5E. Fn-EDA partially contributes to myeloid cell α9-mediated stroke exacerbation. A, Schematic of experimental design. B, Left: Representative magnetic resonance imaging from 1 mouse of each group on day 1. White is the infarct area. Right: Corrected mean infarct volumes of each genotype. n=10, 10, 10, and 11. C, Neurological outcome (Bederson score) from each genotype as assessed on day 1 (higher score indicates a worse outcome, n=10, 10, 10, and 11). D, The survival rate after 60 min transient ischemia. E, Modified Neurological Severity Score (mNSS) at days 1, 3, and 7 based on spontaneous activity, symmetry in the movement of 4 limbs, forepaw outstretching, climbing, body proprioception, and responses to vibrissae touch (higher score indicates a better outcome). n=10, 10, 8, 9, 5, 6 and 10, 11, 5, 10, 3, 6. Data are mean±SEM (B) and median±range (C and E). Statistical analysis: 2-way ANOVA followed by Fisher LSD multiple comparisons test (B), Mann-Whitney test (C) Comparison of survival curves was evaluated by log-rank (Mantel-Cox) test (D), Kruskal-Wallis test followed by Fisher LSD multiple comparisons test (E). MCAO indicates middle cerebral artery occlusion.

DETAILED DESCRIPTION OF THE INVENTION

Inhibitor of Integrin α9β1

Figures 2A, 2B, 2C, 2D, 2E, 2F, 2G, 2H, 2I:
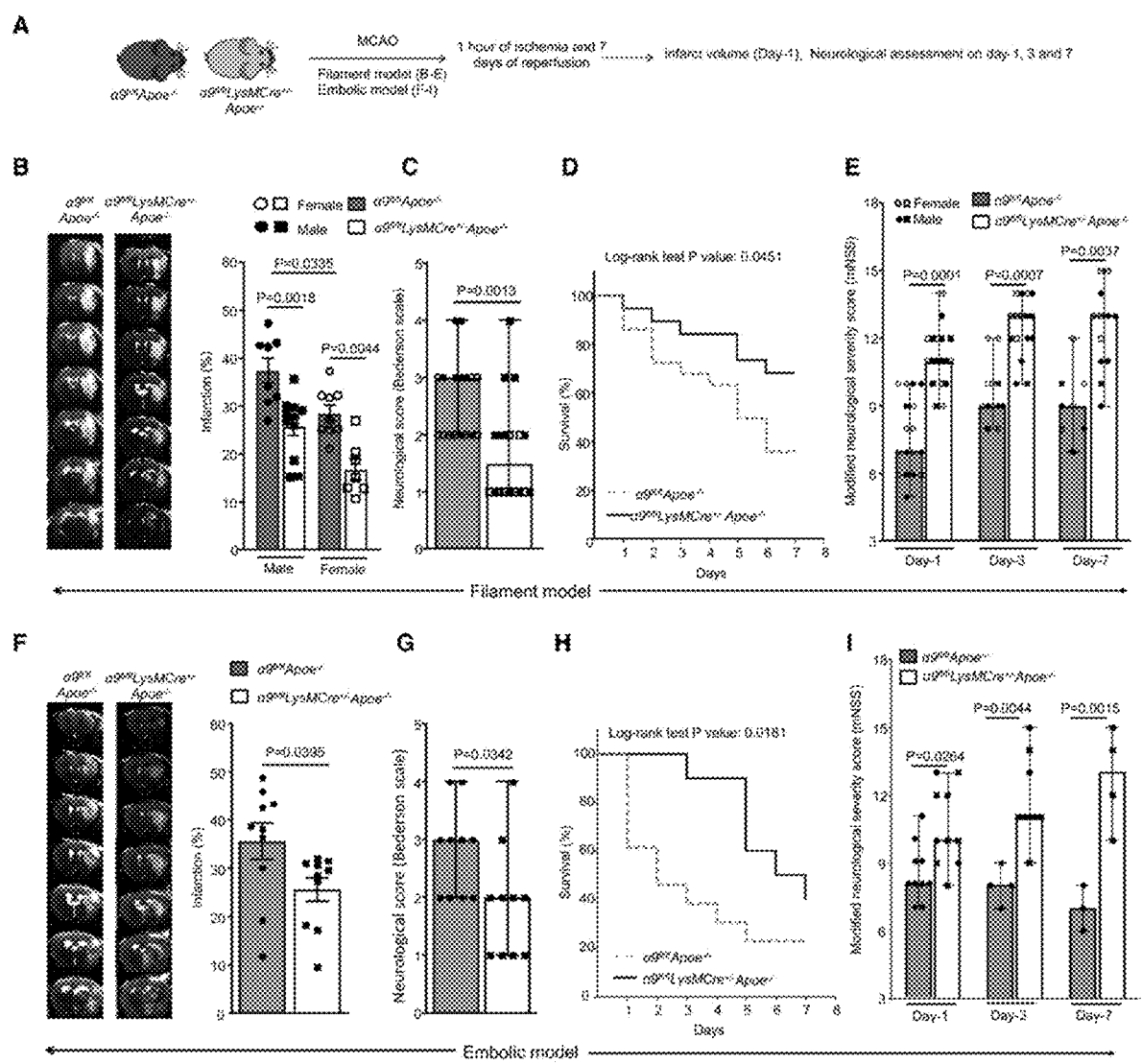
FIGS. 2A-2I. Deletion of integrin α9 in myeloid cells improves stroke outcome in preexisting comorbid condition of hyperlipidemia. A. Schematic of experimental design. B. Left: Representative magnetic resonance imaging from one mouse of each genotype on day 1 in filament model. White is the infarct area. Right: Corrected mean infarct volumes of each genotype, n=17 and 18. C. Neurological outcome (Bederson score) from each genotype as assessed on day 1 (higher score indicates worse outcome). D. Survival rate between day 0 to day 7 after 60 min transient ischemia in filament model. E. Modified Neurological Severity Score (mNSS) at days 1, 3, and 7 in filament model based on spontaneous activity, symmetry in the movement of 4 limbs, forepaw outstretching, climbing, body proprioception and responses to vibrissae touch (higher score indicates a better outcome). N=17, 18, 12, 16, 8 and 12. F, G, H and I. Infarction (%, n=1- and 10)), Bederson score (n=10 and 10), survival rate (%) and mNSS (n=10, 10, 4, 9, 3 and 4) in embolic model. Only male mice were used in embolic model. Data are mean±SEM (B and F) and median±range (C, G, E and I). Statistical analysis: 2-way ANOVA followed by Fisher LSD multiple comparisons test (B), unpaired t test (F), Mann-Whitney test (C and G), Comparison of survival curves was evaluated by log-rank (Mantel-Cox) test (D and H), Kruskal-Wallis test followed by Fisher's LSD multiple comparisons test (E and I). MCAO indicates middle cerebral artery occlusion.

The term "inhibitor of integrin α9β1" as used herein refers to an inhibitor that is capable of inhibiting the function of integrin α9β1. In certain aspects, the present invention provides a method of inhibiting integrin α9β1 activity, comprising contacting integrin α9β1 or a binding partner of integrin α9β1 with an isolated anti-integrin α9 inhibitor, wherein the integrin α9β1 activity is inhibited. In certain embodiments, the inhibition is accomplished by inhibiting the binding of integrin α9 to other ligands. In certain embodiments, the inhibition is accomplished by inhibiting the downstream signaling pathway of integrin α9 activation.

For example, in certain embodiments, the inhibitor detectably inhibits the biological activity of integrin α9β1 as measured. In certain embodiments, the inhibitor inhibits the biological activity of integrin α9β1 by at least about 5%, at least about 10%, at least about 20%, at least about 30%, at least about 40%, at least about 50%, at least about 60%, at least about 70%, at least about 80%, or at least about 90%. In certain embodiments, the inhibitor is a selective inhibitor of integrin α9β1. For example, the inhibitor is an antibody that is at least 5, at least 10, at least 50, at least 100, at least 500, or at least 1,000 fold selective for integrin α9β1 over another integrin in a selected assay.

In certain aspects, the present invention provides a method of inhibiting the activity of integrin α9β1, comprising contacting integrin α9β1 with an isolated anti-integrin α9 inhibitor.

In certain embodiments, the inhibitor is a peptide against its binding partner. In certain embodiments, the peptide is Vascular endothelial growth factor (VEGF), Vascular cell adhesion molecule 1 (VCAM-1), tenascin C, osteopontin, fibronectin-EDA, thrombospondin-1 or disintegrin VLO5. In certain embodiments, the Fn-EDA peptide comprises or consists of SEQ ID NO:1 (CTYSSPEDGIHEC). In certain embodiments, the Tenascin-C peptide comprises or consists of SEQ ID NO:2 (PLAEIDGIELTY).

In certain embodiments, the anti-integrin α9 inhibitor is an antibody or fragment thereof. In certain embodiments, the inhibitor is an antibody. In certain embodiments, the antibody is anti-integrin α9 Ig 55A2C. See U.S. Pat. Nos. 8,821,863; 8,715,655; 8,221,754 and 7,595,045.

The invention encompasses isolated or substantially purified protein compositions. As used herein, the terms "protein," "peptide" and "polypeptide" are used interchangeably herein. In the context of the present invention, an "isolated" or "purified" polypeptide is a polypeptide that exists apart from its native environment and is therefore not a product of nature. An isolated polypeptide may exist in a purified form or may exist in a non-native environment such as, for example, a transgenic host cell. For example, an "isolated" or "purified" protein, or biologically active portion thereof, is substantially free of other cellular material, or culture medium when produced by recombinant techniques, or substantially free of chemical precursors or other chemicals when chemically synthesized. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, culture medium may represent less than about 30%, 20%, 10%, or 5% (by dry weight) of chemical precursors or non-protein-of-interest chemicals. Fragments and variants of the disclosed proteins or partial-length proteins encoded thereby are also encompassed by the present invention. By "fragment" or "portion" is meant a full length or less than full length of the amino acid sequence of a polypeptide or protein.

"Naturally occurring" is used to describe an object that can be found in nature as distinct from being artificially produced. For example, a protein present in an organism (including a virus), which can be isolated from a source in nature and which has not been intentionally modified by man in the laboratory, is naturally occurring.

A "variant" of a molecule is a sequence that is substantially similar to the sequence of the native molecule.

As used herein, "sequence identity" or "identity" in the context of two polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated.

The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to the reference sequence over a specified comparison window. Optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may results form, for example, genetic polymorphism or from human manipulation. Methods for such manipulations are generally known in the art.

Thus, the polypeptides of the invention may be altered in various ways including amino acid substitutions, deletions, truncations, and insertions. Methods for such manipulations are generally known in the art. Conservative substitutions, such as exchanging one amino acid with another having similar properties, are preferred.

The polypeptides of the invention encompass naturally occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations."

As used herein, the term "antibody" includes a single-chain variable fragment (scFv or "nanobody"), humanized, fully human or chimeric antibodies, single-chain antibodies, diabodies, and antigen-binding fragments of antibodies that do not contain the Fc region (e.g., Fab fragments). In certain embodiments, the antibody is a human antibody or a humanized antibody. A "humanized" antibody contains only the three CDRs (complementarity determining regions) and sometimes a few carefully selected "framework" residues (the non-CDR portions of the variable regions) from each donor antibody variable region recombinantly linked onto the corresponding frameworks and constant regions of a human antibody sequence. A "fully humanized antibody" is created in a hybridoma from mice genetically engineered to have only human-derived antibody genes or by selection from a phage-display library of human-derived antibody genes.

A scFv is a fusion protein of the variable region of the heavy ($V_H$) and light chains ($V_L$) of an immunoglobulin that is connected by means of a linker peptide. The linker is usually short, about 10-25 amino acids in length. If flexibility is important, the linker will contain a significant number of glycines. If solubility is important, serines or theonines will be utilized in the linker. The linker may link the amino-terminus of the $V_H$ to the carboxy-terminus of the $V_L$, or the linker may link the carboxy-terminus of the $V_H$ to the amino-terminus of the $V_L$. Divalent (also called bivalent) scFvs can be generated by linking two scFvs. For example, a divalent scFv can be made by generating a single peptide containing two $V_H$ and two $V_L$ regions. Alternatively, two peptides, each containing a single $V_H$ and a single $V_L$ region can be dimerized (also called "diabodies"). Holliger et al., "Diabodies: small bivalent and bispecific antibody fragments," PNAS, July 1993, 90:6444-6448. Bivalency allows antibodies to bind to multimeric antigens with high avidity, and bispecificity allows the cross-linking of two antigens.

As used herein, the term "monoclonal antibody" refers to an antibody obtained from a group of substantially homogeneous antibodies, that is, an antibody group wherein the antibodies constituting the group are homogeneous except for naturally occurring mutants that exist in a small amount. Monoclonal antibodies are highly specific and interact with a single antigenic site. Furthermore, each monoclonal antibody targets a single antigenic determinant (epitope) on an antigen, as compared to common polyclonal antibody preparations that typically contain various antibodies against diverse antigenic determinants. In addition to their specificity, monoclonal antibodies are advantageous in that they are typically produced from hybridoma cultures not contaminated with other immunoglobulins.

The adjective "monoclonal" indicates a characteristic of antibodies obtained from a substantially homogeneous group of antibodies, and does not specify antibodies produced by a particular method. For example, a monoclonal antibody to be used in the present invention can be produced by, for example, hybridoma methods (Kohler and Milstein, Nature 256:495, 1975) or recombination methods (U.S. Pat. No. 4,816,567). The monoclonal antibodies used in the present invention can be also isolated from a phage antibody library (Clackson et al., Nature 352:624-628, 1991; Marks et al., J. Mol. Biol. 222:581-597, 1991). The monoclonal antibodies of the present invention may comprise "chimeric" antibodies (immunoglobulins), wherein a part of a heavy (H) chain and/or light (L) chain is derived from a specific species or a specific antibody class or subclass, and the remaining portion of the chain is derived from another species, or another antibody class or subclass. Furthermore, mutant antibodies and antibody fragments thereof are also comprised in the present invention (U.S. Pat. No. 4,816,567; Morrison et al., Proc. Natl. Acad. Sci. USA 81:6851-6855, 1984).

As used herein, the term "mutant antibody" refers to an antibody comprising a variant amino acid sequence in which one or more amino acid residues have been altered. For example, the variable region of an antibody can be modified to improve its biological properties, such as antigen binding. Such modifications can be achieved by site-directed mutagenesis (see Kunkel, Proc. Natl. Acad. Sci. USA 82: 488 (1985)), PCR-based mutagenesis, cassette mutagenesis, and the like. Such mutants comprise an amino acid sequence which is at least 70% identical to the amino acid sequence of a heavy or light chain variable region of the antibody, more specifically at least 75%, even more specifically at least 80%, still more specifically at least 85%, yet more specifically at least 90%, and most specifically at least 95% identical. As used herein, the term "sequence identity" is defined as the percentage of residues identical to those in the antibody's original amino acid sequence, determined after the sequences are aligned and gaps are appropriately introduced to maximize the sequence identity as necessary.

Specifically, the identity of one nucleotide sequence or amino acid sequence to another can be determined using the algorithm BLAST, by Karlin and Altschul (Proc. Natl. Acad. Sci. USA, 90: 5873-5877, 1993). Programs such as BLASTN and BLASTX were developed based on this algorithm (Altschul et al., J. Mol. Biol. 215: 403-410, 1990). To analyze nucleotide sequences according to BLASTN based on BLAST, the parameters are set, for example, as score=100 and wordlength=12. On the other hand, parameters used for the analysis of amino acid sequences by BLASTX based on BLAST include, for example, score=50 and wordlength=3. Default parameters for each program are used when using the BLAST and Gapped BLAST programs. Specific techniques for such analyses are known in the art (see the website of the National Center for Biotechnology Information (NCBI), Basic Local Alignment Search Tool (BLAST)).

Polyclonal and monoclonal antibodies can be prepared by methods known to those skilled in the art.

In another embodiment, antibodies or antibody fragments can be isolated from an antibody phage library, produced by using the technique reported by McCafferty et al. (Nature 348:552-554 (1990)). Clackson et al. (Nature 352:624-628 (1991)) and Marks et al. (J. Mol. Biol. 222:581-597 (1991)) reported on the respective isolation of mouse and human antibodies from phage libraries. There are also reports that describe the production of high affinity (nM range) human antibodies based on chain shuffling (Marks et al., Bio/Technology 10:779-783 (1992)), and combinatorial infection and in vivo recombination, which are methods for constructing large-scale phage libraries (Waterhouse et al., Nucleic Acids Res. 21:2265-2266 (1993)). These technologies can also be used to isolate monoclonal antibodies, instead of using conventional hybridoma technology for monoclonal antibody production.

Antibodies to be used in the present invention can be purified by a method appropriately selected from known methods, such as the protein A-Sepharose method, hydroxyapatite chromatography, salting-out method with sulfate, ion exchange chromatography, and affinity chromatography, or by the combined use of the same.

The present invention may use recombinant antibodies, produced by gene engineering. The genes encoding the antibodies obtained by a method described above are isolated from the hybridomas. The genes are inserted into an appropriate vector, and then introduced into a host (see, e.g., Carl, A. K. Borrebaeck, James, W. Larrick, Therapeutic Monoclonal Antibodies, Published in the United Kingdom by Macmillan Publishers Ltd, 1990). The present invention provides the nucleic acids encoding the antibodies of the present invention, and vectors comprising these nucleic acids. Specifically, using a reverse transcriptase, cDNAs encoding the variable regions (V regions) of the antibodies are synthesized from the mRNAs of hybridomas. After obtaining the DNAs encoding the variable regions of antibodies of interest, they are ligated with DNAs encoding desired constant regions (C regions) of the antibodies, and the resulting DNA constructs are inserted into expression vectors. Alternatively, the DNAs encoding the variable regions of the antibodies may be inserted into expression vectors comprising the DNAs of the antibody C regions. These are inserted into expression vectors so that the genes are expressed under the regulation of an expression regulatory region, for example, an enhancer and promoter. Then, host cells are transformed with the expression vectors to express the antibodies. The present invention provides cells expressing antibodies of the present invention. The cells expressing antibodies of the present invention include cells and hybridomas transformed with a gene of such an antibody.

The antibodies of the present invention also include antibodies which comprise complementarity-determining regions (CDRs), or regions functionally equivalent to CDRs. The term "functionally equivalent" refers to comprising amino acid sequences similar to the amino acid sequences of CDRs of any of the monoclonal antibodies isolated in the Examples. The term "CDR" refers to a region in an antibody variable region (also called "V region"), and determines the specificity of antigen binding. The H chain and L chain each have three CDRs, designated from the N terminus as CDR1, CDR2, and CDR3. There are four regions flanking these CDRs: these regions are referred to as "framework," and their amino acid sequences are highly conserved. The CDRs can be transplanted into other antibodies, and thus a recombinant antibody can be prepared by combining CDRs with the framework of a desired antibody. One or more amino acids of a CDR can be modified without losing the ability to bind to its antigen. For example, one or more amino acids in a CDR can be substituted, deleted, and/or added.

In certain embodiments, an amino acid residue is mutated into one that allows the properties of the amino acid side-chain to be conserved. Examples of the properties of amino acid side chains comprise: hydrophobic amino acids (A, I, L, M, F, P, W, Y, V), hydrophilic amino acids (R, D, N, C, E, Q, G, H, K, S, T), and amino acids comprising the following side chains: aliphatic side-chains (G, A, V, L, I, P); hydroxyl group-containing side-chains (S, T, Y); sulfur atom-containing side-chains (C, M); carboxylic acid- and amide-containing side-chains (D, N, E, Q); base-containing side-chains (R, K, H); and aromatic-containing side-chains (H, F, Y, W). The letters within parenthesis indicate the one-letter amino acid codes. Amino acid substitutions within each group are called conservative substitutions. It is well known that a polypeptide comprising a modified amino acid sequence in which one or more amino acid residues is deleted, added, and/or substituted can retain the original biological activity (Mark D. F. et al., Proc. Natl. Acad. Sci. U.S.A. 81:5662-5666 (1984); Zoller M. J. and Smith M., Nucleic Acids Res. 10: 6487-6500 (1982); Wang A. et al., Science 224: 1431-1433; Dalbadie-McFarland G. et al., Proc. Natl. Acad. Sci. U.S.A. 79: 6409-6413 (1982)). The number of mutated amino acids is not limited, but in general, the number falls within 40% of amino acids of each CDR, and specifically within 35%, and still more specifically within 30% (e.g., within 25%). The identity of amino acid sequences can be determined as described herein.

In the present invention, recombinant antibodies artificially modified to reduce heterologous antigenicity against humans can be used. Examples include chimeric antibodies and humanized antibodies. These modified antibodies can be produced using known methods. A chimeric antibody includes an antibody comprising variable and constant regions of species that are different to each other, for example, an antibody comprising the antibody heavy chain and light chain variable regions of a nonhuman mammal such as a mouse, and the antibody heavy chain and light chain constant regions of a human. Such an antibody can be obtained by (1) ligating a DNA encoding a variable region of a mouse antibody to a DNA encoding a constant region of a human antibody; (2) incorporating this into an expression vector; and (3) introducing the vector into a host for production of the antibody.

A humanized antibody, which is also called a reshaped human antibody, may be obtained by substituting an H or L chain complementarity determining region (CDR) of an antibody of a nonhuman mammal such as a mouse, with the CDR of a human antibody. Conventional genetic recombination techniques for the preparation of such antibodies are known (see, for example, Jones et al., Nature 321: 522-525 (1986); Reichmann et al., Nature 332: 323-329 (1988); Presta Curr. Op. Struct. Biol. 2: 593-596 (1992)). Specifically, a DNA sequence designed to ligate a CDR of a mouse antibody with the framework regions (FRs) of a human antibody is synthesized by PCR, using several oligonucleotides constructed to comprise overlapping portions at their ends. A humanized antibody can be obtained by (1) ligating the resulting DNA to a DNA that encodes a human antibody constant region; (2) incorporating this into an expression vector; and (3) transfecting the vector into a host to produce the antibody (see, European Patent Application No. EP 239,400, and International Patent Application No. WO 96/02576). Human antibody FRs that are ligated via the CDR are selected where the CDR forms a favorable antigen-binding site. The humanized antibody may comprise additional amino acid residue(s) that are not included in the CDRs introduced into the recipient antibody, nor in the framework sequences. Such amino acid residues are usually introduced to more accurately optimize the antibody's ability to recognize and bind to an antigen. For example, as necessary, amino acids in the framework region of an antibody variable region may be substituted such that the CDR of a reshaped human antibody forms an appropriate antigen-binding site (Sato, K. et al., Cancer Res. (1993) 53, 851-856).

Additionally, an antibody of the invention may also be a recombinant antibody (e.g., a humanized or chimeric antibody) or a fragment thereof. Accordingly, such an antibody of the invention or fragment thereof would not be a product of nature. Additionally, an antibody of the invention or a fragment thereof may comprise markedly different characteristics (e.g., structural, functional and/or other properties) as compared to naturally occurring antibody.

The isotypes of the antibodies of the present invention are not limited. The isotypes include, for example, IgG (IgG1, IgG2, IgG3, and IgG4), IgM, IgA (IgA1 and IgA2), IgD, and IgE. The antibodies of the present invention may also be antibody fragments comprising a portion responsible for antigen binding, or a modified fragment thereof. The term "antibody fragment" refers to a portion of a full-length antibody, and generally to a fragment comprising an antigen-binding domain or a variable region. Such antibody fragments include, for example, Fab, F(ab')$_2$, Fv, single-chain Fv (scFv) which comprises a heavy chain Fv and a light chain Fv coupled together with an appropriate linker, diabody (diabodies), linear antibodies, and multispecific antibodies prepared from antibody fragments. Previously, antibody fragments were produced by digesting natural antibodies with a protease; currently, methods for expressing them as recombinant antibodies using genetic engineering techniques are also known (see Morimoto et al., Journal of Biochemical and Biophysical Methods 24:107-117 (1992); Brennan et al., Science 229:81 (1985); Co, M. S. et al., J. Immunol., 1994, 152, 2968-2976; Better, M. & Horwitz, A. H., Methods in Enzymology, 1989, 178, 476-496, Academic Press, Inc.; Plueckthun, A. & Skerra, A., Methods in Enzymology, 1989, 178, 476-496, Academic Press, Inc.; Lamoyi, E., Methods in Enzymology, 1989, 121, 663-669; Bird, R. E. et al., TIBTECH, 1991, 9, 132-137).

An "Fv" fragment is the smallest antibody fragment, and contains a complete antigen recognition site and a binding site. This region is a dimer ($V_H$-$V_L$ dimer) wherein the variable regions of each of the heavy chain and light chain are strongly connected by a noncovalent bond. The three CDRs of each of the variable regions interact with each other to form an antigen-binding site on the surface of the $V_H$-$V_L$ dimer. In other words, a total of six CDRs from the heavy and light chains function together as an antibody's antigen-binding site. However, a variable region (or a half Fv, which contains only three antigen-specific CDRS) alone is also known to be able to recognize and bind to an antigen, although its affinity is lower than the affinity of the entire binding site. Thus, a specific antibody fragment of the present invention is an Fv fragment, but is not limited thereto. Such an antibody fragment may be a polypeptide which comprises an antibody fragment of heavy or light chain CDRs which are conserved, and which can recognize and bind its antigen.

A Fab fragment (also referred to as F(ab)) also contains a light chain constant region and heavy chain constant region (CH1). For example, papain digestion of an antibody produces the two kinds of fragments: an antigen-binding fragment, called a Fab fragment, containing the variable regions of a heavy chain and light chain, which serve as a single antigen-binding domain; and the remaining portion, which is called an "Fc" because it is readily crystallized. A Fab' fragment is different from a Fab fragment in that a Fab' fragment also has several residues derived from the carboxyl terminus of a heavy chain CH1 region, which contains one or more cysteine residues from the hinge region of an antibody. A Fab' fragment is, however, structurally equivalent to Fab in that both are antigen-binding fragments which comprise the variable regions of a heavy chain and light chain, which serve as a single antigen-binding domain. Herein, an antigen-binding fragment comprising the variable regions of a heavy chain and light chain which serve as a single antigen-binding domain, and which is equivalent to that obtained by papain digestion, is referred to as a "Fab-like antibody," even when it is not identical to an antibody fragment produced by protease digestion. Fab'-SH is Fab' with one or more cysteine residues having free thiol groups in its constant region. A F(ab') fragment is produced by cleaving the disulfide bond between the cysteine residues in the hinge region of F(ab')$_2$. Other chemically crosslinked antibody fragments are also known to those skilled in the art. Pepsin digestion of an antibody yields two fragments; one is a F(ab')$_2$ fragment which comprises two antigen-binding domains and can cross-react with antigens, and the other is the remaining fragment (referred to as pFc'). Herein, an antibody fragment equivalent to that obtained by pepsin digestion is referred to as a "F(ab')$_2$-like antibody" when it comprises two antigen-binding domains and can cross-react with antigens. Such antibody fragments can also be produced, for example, by genetic engineering. Such antibody fragments can also be isolated, for example, from the antibody phage library described above. Alternatively, F(ab')$_2$-SH fragments can be recovered directly from hosts, such as E. coli, and then allowed to form F(ab')$_2$ fragments by chemical crosslinking (Carter et al., Bio/Technology 10:163-167 (1992)). In an alternative method, F(ab')$_2$ fragments can be isolated directly from a culture of recombinant hosts.

The term "diabody (db)" refers to a bivalent antibody fragment constructed by gene fusion (for example, P. Holliger et al., Proc. Natl. Acad. Sci. USA 90: 6444-6448 (1993), EP 404,097, WO 93/11161). In general, a diabody is a dimer of two polypeptide chains. In the each of the polypeptide chains, a light chain variable region ($V_L$) and a heavy chain variable region ($V_H$) in an identical chain are connected via a short linker, for example, a linker of about five residues, so that they cannot bind together. Because the linker between the two is too short, the $V_L$ and $V_H$ in the same polypeptide chain cannot form a single chain V region fragment, but instead form a dimer. Thus, a diabody has two antigen-binding domains. When the $V_L$ and $V_H$ regions against the two types of antigens (a and b) are combined to form $V_{La}$-$V_{Hb}$ and $V_{Lb}$-$V_{Ha}$ via a linker of about five residues, and then co-expressed, they are secreted as bispecific Dbs. The antibodies of the present invention may be such Dbs.

A single-chain antibody (also referred to as "scFv") can be prepared by linking a heavy chain V region and a light chain V region of an antibody (for a review of scFv see Pluckthun "The Pharmacology of Monoclonal Antibodies" Vol. 113, eds. Rosenburg and Moore, Springer Verlag, N.Y., pp. 269-315 (1994)). Methods for preparing single-chain antibodies are known in the art (see, for example, U.S. Pat. Nos. 4,946,778; 5,260,203; 5,091,513; and 5,455,030). In such scFvs, the heavy chain V region and the light chain V region are linked together via a linker, such as a polypeptide linker (Huston, J. S. et al., Proc. Natl. Acad. Sci. U.S.A, 1988, 85, 5879-5883). The heavy chain V region and the light chain V region in a scFv may be derived from the same antibody, or from different antibodies. The peptide linker used to ligate the V regions may be any single-chain peptide consisting of 12 to 19 residues. A DNA encoding a scFv can be amplified by PCR using, as a template, either the entire DNA, or a partial DNA encoding a desired amino acid sequence, selected from a DNA encoding the heavy chain or the V region of the heavy chain of the above antibody, and a DNA encoding the light chain or the V region of the light chain of the above antibody; and using a primer pair that defines the two ends. Further amplification can be subsequently conducted using a combination of the DNA encoding the peptide linker portion, and the primer pair that defines both ends of the DNA to be ligated to the heavy and light chain respectively. After constructing DNAs encoding scFvs, conventional methods can be used to obtain expression vectors comprising these DNAs, and hosts transformed by these expression vectors. Furthermore, scFvs can be obtained according to conventional methods using the resulting hosts. These antibody fragments can be produced in hosts by obtaining genes that encode the antibody fragments and expressing these as outlined above. Antibodies bound to various types of molecules, such as polyethylene glycols (PEGs), may be used as modified antibodies. Methods for modifying antibodies are already established in the art. The term "antibody" in the present invention also encompasses the above-described antibodies.

The antibodies obtained can be purified to homogeneity. The antibodies can be isolated and purified by a method routinely used to isolate and purify proteins. The antibodies can be isolated and purified by the combined use of one or more methods appropriately selected from column chromatography, filtration, ultrafiltration, salting out, dialysis, preparative polyacrylamide gel electrophoresis, and isoelectrofocusing, for example (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory, 1988). Such methods are not limited to those listed above. Chromatographic methods include affinity chromatography, ion exchange chromatography, hydrophobic chromatography, gel filtration, reverse-phase chromatography, and adsorption chromatography. These chromatographic methods can be practiced using liquid phase chromatography, such as HPLC and FPLC. Columns to be used in affinity chromatography include protein A columns and protein G columns. For example, protein A columns include Hyper D, POROS, and Sepharose F. F. (Pharmacia). Antibodies can also be purified by utilizing antigen binding, using carriers on which antigens have been immobilized.

The antibodies of the present invention can be formulated according to standard methods (see, for example, Remington's Pharmaceutical Science, latest edition, Mark Publishing Company, Easton, U.S.A), and may comprise pharmaceutically acceptable carriers and/or additives. The present invention relates to compositions (including reagents and pharmaceuticals) comprising the antibodies of the invention, and pharmaceutically acceptable carriers and/or additives. Exemplary carriers include surfactants (for example, PEG and Tween), excipients, antioxidants (for example, ascorbic acid), coloring agents, flavoring agents, preservatives, stabilizers, buffering agents (for example, phosphoric acid, citric acid, and other organic acids), chelating agents (for example, EDTA), suspending agents, isotonizing agents, binders, disintegrators, lubricants, fluidity promoters, and corrigents. However, the carriers that may be employed in the present invention are not limited to this list. In fact, other commonly used carriers can be appropriately employed: light anhydrous silicic acid, lactose, crystalline cellulose, mannitol, starch, carmelose calcium, carmelose sodium, hydroxypropylcellulose, hydroxypropylmethyl cellulose, polyvinylacetaldiethylaminoacetate, polyvinylpyrrolidone, gelatin, medium chain fatty acid triglyceride, polyoxyethylene hydrogenated castor oil 60, sucrose, carboxymethylcellulose, corn starch, inorganic salt, and so on. The composition may also comprise other low-molecular-weight polypeptides, proteins such as serum albumin, gelatin, and immunoglobulin, and amino acids such as glycine, glutamine, asparagine, arginine, and lysine. When the composition is prepared as an aqueous solution for injection, it can comprise an isotonic solution comprising, for example, physiological saline, dextrose, and other adjuvants, including, for example, D-sorbitol, D-mannose, D-mannitol, and sodium chloride, which can also contain an appropriate solubilizing agent, for example, alcohol (for example, ethanol), polyalcohol (for example, propylene glycol and PEG), and non-ionic detergent (polysorbate 80 and HCO-50).

If necessary, antibodies of the present invention may be encapsulated in microcapsules (microcapsules made of hydroxycellulose, gelatin, polymethylmethacrylate, and the like), and made into components of colloidal drug delivery systems (liposomes, albumin microspheres, microemulsions, nano-particles, and nano-capsules) (for example, see "Remington's Pharmaceutical Science 16th edition", Oslo Ed. (1980)). Moreover, methods for making sustained-release drugs are known, and these can be applied for the antibodies of the present invention (Langer et al., J. Biomed. Mater. Res. 15: 167-277 (1981); Langer, Chem. Tech. 12: 98-105 (1982); U.S. Pat. No. 3,773,919; EP Patent Application No. 58,481; Sidman et al., Biopolymers 22: 547-556 (1983); EP: 133,988)).

Methods of Use

In certain aspects, the present invention provides a method of inhibiting integrin α9β1 activity, comprising contacting integrin α9β1 or a binding partner of integrin α9β1 with an isolated anti-integrin α9 inhibitor, wherein the integrin α9β1 activity is inhibited.

Certain embodiments provide a method of inhibiting the activity of integrin α9β1, comprising contacting integrin α9β1 with an isolated anti-integrin α9 inhibitor as described herein. In certain embodiments, the integrin α9β1 or the binding partner of integrin α9β1 is contacted in vitro. In certain embodiments, the integrin α9β1 or the binding partner of integrin α9β1 is contacted in vivo. Methods for measuring the activity of integrin α9β1 are known in the art. In certain embodiments, an anti-integrin α9 inhibitor inhibits the binding of integrin α9 to other ligands (such as Fibronectin EDA, tenascin C, thrombospondin-1), or the downstream signaling pathway of integrin α 9 activation, by at least about 5%, at least about 10%, at least about 15%, at least about 20%, at least about 25%, at least about 30%, at least about 40%, at least about 50%, at least about 60%, at least about 70%, at least about 80%, at least about 90%.

In certain embodiments, the activity of the integrin α9β1 is inhibited by at least about 25% as compared to a control.

In certain embodiments, the activity of the integrin α9β1 is inhibited by at least about 40% as compared to a control.

In certain aspects, the present invention provides a method for treating integrin α9β1-related condition in a mammal, comprising administering an effective amount of an isolated anti-integrin α9 inhibitor to the mammal.

In certain embodiments, the anti-integrin α9 inhibitor is administered intravenously or intraperitoneally by infusion or injection.

In certain embodiments, the anti-integrin α9 inhibitor is administered by local injection.

In certain embodiments, the method further comprises administering at least one additional therapeutic agent to the mammal. In certain embodiments, the at least one additional therapeutic agent is useful for treating pain. In certain embodiments, the at least one additional therapeutic agent is a steroid, a non-steroid anti-inflammatory drug (NSAIDs), gabapentin, Lyrica, a local anesthetic (e.g., lidocaine) or an opioid.

In certain aspects, the present invention provides an isolated anti-integrin α9 inhibitor for the prophylactic or therapeutic treatment of an integrin α9β1-related condition.

In certain aspects, the present invention provides a use of an isolated anti-integrin α9 inhibitor to prepare a medicament for the treatment of an integrin α9β1-related condition in a mammal.

In certain embodiments, the inhibitor is a peptide. In certain embodiments, the inhibitor is a peptide against its binding partner. In certain embodiments, the peptide is Vascular endothelial growth factor (VEGF), Vascular cell adhesion molecule 1 (VCAM-1), tenascin C, osteopontin, fibronectin-EDA, thrombospondin-1 or disintegrin VLO5. In certain embodiments, the Fn-EDA peptide comprises or consists of SEQ ID NO:1 (CTYSSPEDGIHEC). In certain embodiments, the Tenascin-C peptide comprises or consists of SEQ ID NO:2 (PLAEIDGIELTY). In certain embodiments, the anti-integrin α9 inhibitor is an antibody or fragment thereof.

In certain embodiments, the inhibitor is an antibody.

In certain embodiments, the antibody is anti-integrin α9 Ig 55A2C.

In certain embodiments, the integrin α9β1-related condition is associated with or results from chemotherapy, nerve injury, trigeminal neuralgia, spinal cord injury, stroke, brain trauma, arthritic pain, headache or migraine pain, cancer or surgery, thrombosis, or inflammation.

In certain embodiments, the stroke is ischemic stroke.

In certain embodiments, the ischemic stroke is acute ischemic stroke.

In certain embodiments, the arthritic pain is osteoarthritis or rheumatoid arthritis pain.

In certain embodiments, the pain is postoperative pain.

In certain embodiments, the integrin α9β1-related condition is thrombosis.

In certain embodiments, the integrin α9β1-related condition is inflammation.

In certain embodiments, the integrin α9β1-related condition is a reperfusion injury.

Administration

For in vivo use, an anti-integrin α9 inhibitor of the invention is generally incorporated into a pharmaceutical composition prior to administration. Within such compositions, one or more anti-integrin α9 inhibitors of the invention may be present as active ingredient(s) (i.e., are present at levels sufficient to provide a statistically significant effect on the symptoms of a relevant disease, as measured using a representative assay). A pharmaceutical composition comprises one or more such anti-integrin α9 inhibitors in combination with any pharmaceutically acceptable carrier(s) known to those skilled in the art to be suitable for the particular mode of administration. In addition, other pharmaceutically active ingredients (including other therapeutic agents) may, but need not, be present within the composition.

The term "therapeutically effective amount," in reference to treating a disease state/condition, refers to an amount of an anti-integrin α9 inhibitor either alone or as contained in a pharmaceutical composition that is capable of having any detectable, positive effect on any symptom, aspect, or characteristics of a disease state/condition when administered as a single dose or in multiple doses. Such effect need not be absolute to be beneficial.

The terms "treat" and "treatment" refer to both therapeutic treatment and prophylactic or preventative measures, wherein the object is to prevent or decrease an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The anti-integrin α9 inhibitor may also be administered intravenously or intraperitoneally by infusion or injection. Additionally, the anti-integrin α9 inhibitor may be administered by local injection, such as by intrathecal injection, epidural injection or peri-neural injection using a scope. Solutions of the anti-integrin α9 inhibitor may be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the anti-integrin α9 inhibitor that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be useful to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the anti-integrin α9 inhibitor in the required amount in the appropriate solvent with various of the other ingredients enumerated above, as required, followed by filter sterilization. In the case of sterile powders for the preparation of sterile injectable solutions, the methods of preparation are vacuum drying and the freeze drying techniques, which yield a powder of the antibody plus any additional desired ingredient present in the previously sterile-filtered solutions.

For topical administration, the present anti-integrin α9 inhibitors may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present anti-integrin α9 inhibitors can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the anti-integrin α9 inhibitors of the present invention can be determined by comparing their in vitro activity, and in vivo activity in animal models. Methods for the extrapolation of effective dosages in mice, and other animals, to humans are known to the art; for example, see U.S. Pat. No. 4,938,949.

The amount of an anti-integrin α9 inhibitor of the present invention required for use in treatment will vary with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Anti-integrin α9 inhibitors of the invention can also be administered in combination with other therapeutic agents and/or treatments, such as other agents or treatments that are useful for the treatment of pain. Non-limiting examples of such agents include steroids, non-steroid anti-inflammatory drugs (NSAIDs), gabapentin, Lyrica, local anesthetics (e.g., lidocaine) and opioids. Additionally, one or more anti-integrin α9 inhibitors of the invention may be administered (e.g., a combination of antibodies, or fragments thereof, may be administered). Accordingly, one embodiment the invention also provides a composition comprising an anti-integrin α9 inhibitor of the invention, at least one other therapeutic agent, and a pharmaceutically acceptable diluent or carrier. The invention also provides a kit comprising an anti-integrin α9 inhibitor of the invention, at least one other therapeutic agent, packaging material, and instructions for administering an anti-integrin α9 inhibitor of the invention and the other therapeutic agent or agents to an animal to inhibit integrin α9β1 activity.

As used herein, the term "therapeutic agent" refers to any agent or material that has a beneficial effect on the mammalian recipient.

As used herein, the term "therapeutic agent" refers to any agent or material that has a beneficial effect on the mammalian recipient. Thus, "therapeutic agent" embraces both therapeutic and prophylactic molecules having nucleic acid or protein components.

"Treating" as used herein refers to ameliorating at least one symptom of, curing and/or preventing the development of a given disease or condition.

Kits

Certain embodiments provide a kit comprising an isolated anti-integrin α9 inhibitor as described herein, packaging material, and instructions for administering the inhibitor, to a mammal to treat an integrin α9β1-related condition. In certain embodiments, the integrin α9β1-related condition is associated with or results from chemotherapy, nerve injury, trigeminal neuralgia, spinal cord injury, stroke, brain trauma, arthritic pain, headache or migraine pain, cancer or surgery, thrombosis, or inflammation.

In certain embodiments, the kit further comprises at least one additional therapeutic agent. In certain embodiments, the at least one additional therapeutic agent is useful for treating pain. In certain embodiments, the at least one additional therapeutic agent is a steroid, a non-steroid anti-inflammatory drug (NSAIDs), gabapentin, Lyrica, a local anesthetic (e.g., lidocaine) or an opioid.

The invention will now be illustrated by the following non-limiting Example.

EXAMPLE

Abstract

Background: Currently, there is no effective intervention to limit brain damage following reperfusion. Clinical studies have shown a positive correlation between an increased influx of neutrophils and the severity of brain injury following reperfusion. Integrin α9β1 is highly expressed on activated neutrophils and contributes to stable adhesion. The role of integrin α9β1 in the progression of ischemic stroke remains unknown.

Methods: We generated and evaluated stroke outcomes in myeloid-specific α9-deficient ($α9^{-/-}$) wild-type ($α9^{fl/fl}$ LysMCre$^{+/-}$), hyperlipidemic ($α9^{fl/fl}$ LysMCre$^{+/-}$Apoe$^{-/-}$) and aged (bone marrow chimeric) mice to evaluate stroke outcome. Littermates were used as controls. Susceptibility to ischemia/reperfusion injury was evaluated in the same mice following 1, 7 and 28 days of reperfusion in two models of experimental stroke: filament and embolic. Quantitative assessment of stroke outcome was evaluated by measuring infarct volume by MRI, cerebral blood flow (CBF) by laser speckle imaging, neurological and sensorimotor outcomes (cylinder, accelerated rota-rod, and adhesive removal tests), and assessment of post-ischemic thrombo-inflammation (fibrin, platelet thrombi, neutrophil, phospho-NF-κB, TNFα, and IL-1β).

Results: It was found that peripheral neutrophils displayed elevated α9 expression following stroke. Irrespective of sex, genetic deletion of α9 in myeloid cells improved short- and long-term stroke outcomes in the wild type, hyperlipidemic, and aged mice. Improved stroke outcome and enhanced survival in myeloid-specific $α9^{-/-}$ mice was because of marked decrease in cerebral thromboinflammatory response as evidenced by reduced fibrin, platelet thrombi, neutrophil, NETosis, and decreased phospho-NF-κB (nuclear factor-κB), TNF (tumor necrosis factor)-α, and IL (interleukin)-1β levels. $\alpha 9^{-/-}$ mice were less susceptible to FeCl3 injury-induced carotid artery thrombosis that was concomitant with improved regional cerebral blood flow following stroke as revealed by laser speckle imaging. Mechanistically, fibronectin containing extra domain A, a ligand for integrin α9, partially contributed to α9-mediated stroke exacerbation. Infusion of a specific anti-integrin α9 inhibitor into hyperlipidemic mice following reperfusion significantly reduced infarct volume and improved short- and long-term functional outcomes up to 28 days.

Conclusion: We provide genetic and pharmacologic evidence that targeting myeloid-specific integrin α9β1 improves short- and long-term functional outcome in stroke models with preexisting comorbidities by limiting cerebral thrombosis and inflammation.

Introduction

Current treatments for ischemic stroke include thrombolysis using tPA (tissue-type plasminogen activator) and mechanical thrombectomy. While reperfusion of ischemic brain regions has shown promising clinical outcomes, evidence from clinical studies and animal models suggest that cerebral reperfusion promotes oxidative stress, secondary thrombosis, and vascular inflammation, which aggravate neuronal death in the ischemic penumbra. Antiplatelet agents, including aspirin, P2Y12 antagonists, and glycoprotein IIb/IIIa inhibitors, can reduce the risk of secondary thrombosis, but they are associated with increased risk of hemorrhagic transformation. At present, there is no effective intervention available that can efficiently reduce brain damage during reperfusion. A better understanding of molecular mechanisms that facilitate ischemia/reperfusion injury may, therefore, result in the development of novel and effective therapeutic regimens for the treatment of acute ischemic stroke with minimal side effects.

Since thrombosis and inflammation (thromboinflammation) mediate reperfusion injury, an ideal therapeutic target would be the one that limits thromboinflammatory responses without causing significant bleeding. Clinical studies have reported a positive correlation between the increased influx of neutrophils and severity of brain injury following reperfusion. Neutrophils potentiate neuronal injury by triggering capillary sludging, secreting inflammatory mediators, generating free radicals, and enhancing thrombosis via the formation of neutrophil-platelet aggregates and neutrophil extracellular traps (NETs). Integrin α9β1, which highly expressed on activated neutrophils, stabilizes neutrophil adhesion to the activated endothelium in synergy with β2 integrin. β1 is the only known subunit of α9. Besides neutrophils, integrin α9β1 is also expressed on several other cells, including monocytes, smooth muscle cells, hepatocytes, endothelial cells, and epithelial cells. Until a few years ago, signaling cascades involving α9β1 were largely overlooked; however, with recent discoveries linking α9β1 to essential processes in physiology and disease, this integrin is now receiving increased attention. The potential mechanistic role of α9β1 in stroke evolution has not been investigated.

Current Stroke Therapy Academic Industry Roundtable (STAIR) recommendations and the National Institutes of Health-National Institute of Neurological Disorders and Stroke (NIH-NINDS) panel consensus for preclinical assessment of novel neuroprotective agents for stroke recommend evaluation of underlying mechanisms for stroke progression, with assessment of response to treatment in at least two different stroke models in both sexes with preexisting comorbidities that adequately mimic the human physiology. Herein, we evaluated the role of myeloid-specific integrin α9 on stroke outcome following the current STAIR guidelines. Novel myeloid-specific $\alpha 9^{-/-}$ mice were generated in wild-type (WT; $\alpha 9^{fl/fl}$ LysMCre$^{+/-}$), hyperlipidemic ($\alpha 9^{fl/fl}$ LysMCre$^{+/-}$Apoe$^{-/-}$) and aged (bone marrow [BM] chimeric) background to determine the mechanistic role of integrin α9 in ischemic stroke outcome. We chose preexisting comorbidities, including hyperlipidemia, because these conditions are known to exacerbate stroke outcome 16 and thereby enhance sensitivity to stroke and worsen sensorimotor deficit. We provide evidence for the first time that myeloid-specific integrin α9 exacerbates short- and long-term stroke outcome in murine stroke model with preexisting comorbidity by promoting thromboinflammation. by promoting thrombo-inflammation.

Methods

Mice

Figure 8:
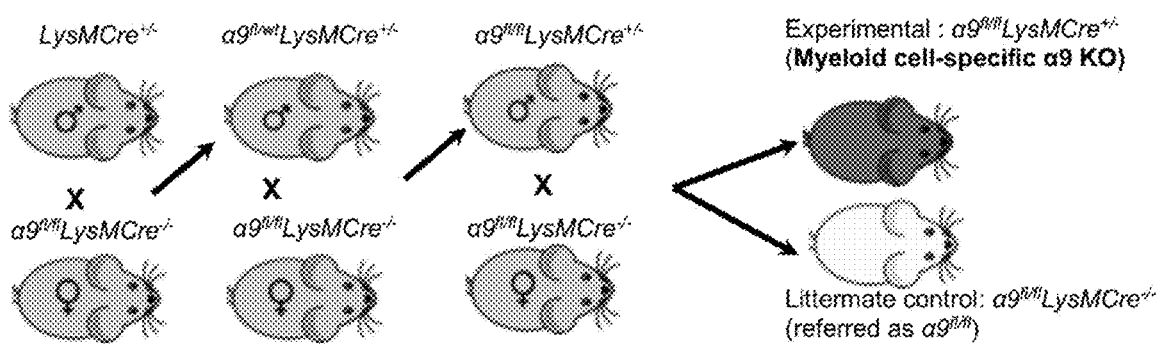
FIG. 8: Schematic showing the strategy to generate myeloid cell-specific integrin α9 deficient mice.
Figure 9A:
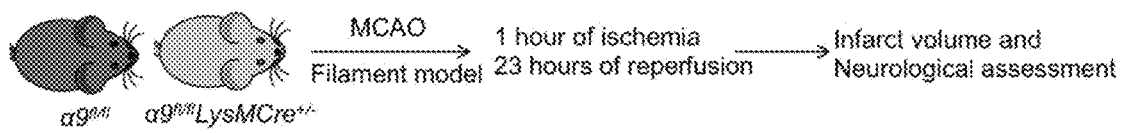
FIGS. 9A-9D: Myeloid-cell specific α9-A mice on a WT background exhibit improved stroke outcome. A. Schematic of experimental design. B. Left: Representative MRI from 1 mouse of each genotype on day 1. White is the infarct area. Right: Corrected mean infarct area of each genotype (n=11, 11, 10, 10). C. Neurological outcome (Bederson score) from each genotype as assessed before sacrifice on day 1 (depicted as scatter plots, including median, n=11, 11, 10, 10). D. Modified Neurological Severity Score (mNSS) at day 1, 3, and 7 based on spontaneous activity, symmetry in the movement of 4 limbs, forepaw outstretching, climbing, body proprioception and responses to vibrissae touch. Higher score indicates a better outcome, n-11,11,10,10. Data are mean±SEM (B), median±range (C and D). Statistical analysis: Two-way ANOVA followed by Fisher's LSD multiple comparisons test (B), Kruskal-Wallis test followed by Fisher's LSD multiple comparisons test (C and D).
Figure 9B:
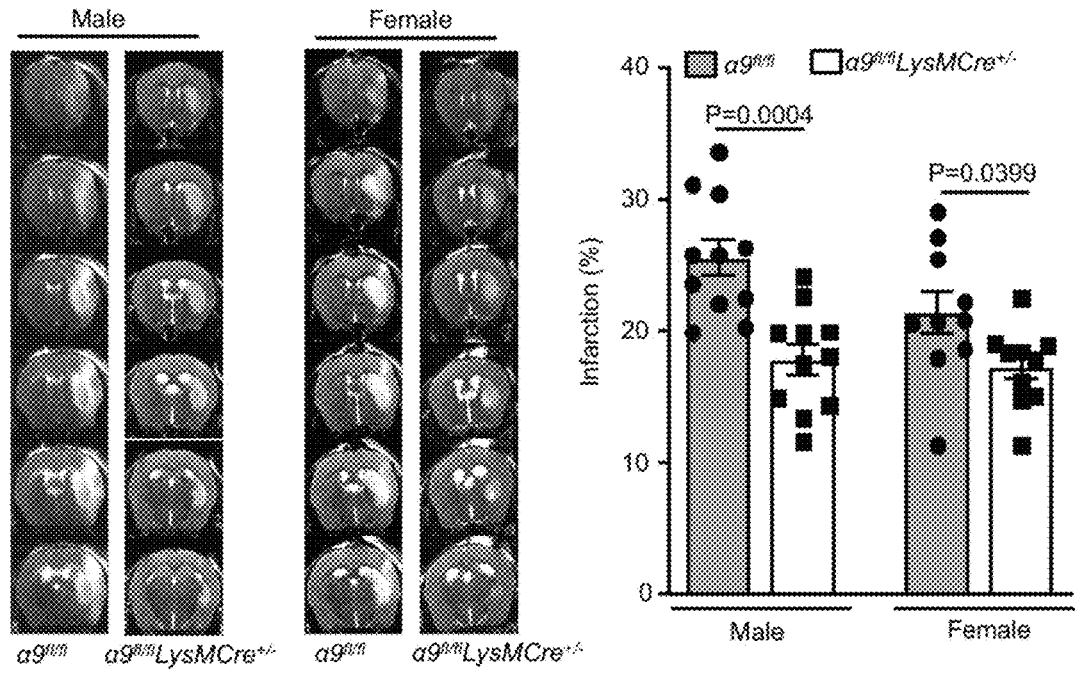
Figure 9C:
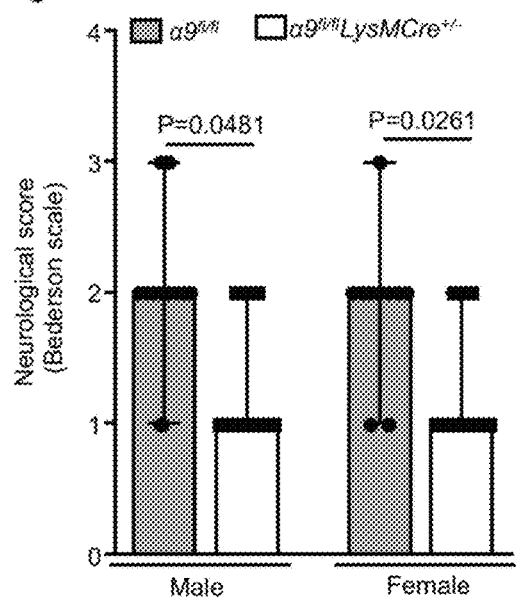
Figure 9D:
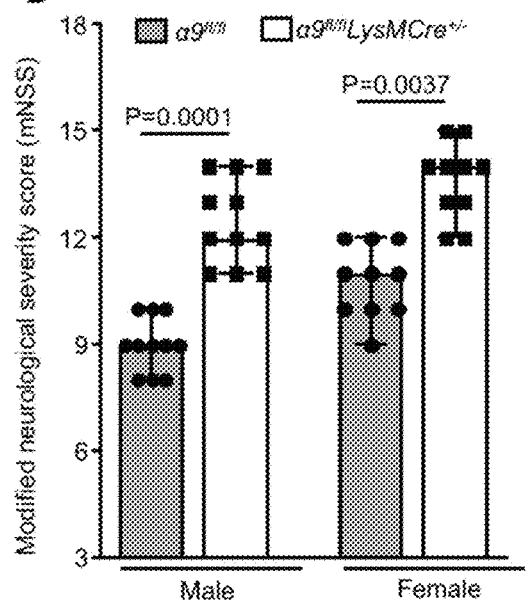

Myeloid specific α9-deficient mice ($\alpha 9^{fl/fl}$ LysMCre$^{+/-}$) were generated by crossing $\alpha 9^{fl/fl}$ mice[16] with LysMCre$^{+/+}$ mice (FIG. 8). To develop myeloid-specific $\alpha 9^{-/-}$ mice on the hyperlipidemic Apoe$^{-/-}$ background ($\alpha 9^{fl/fl}$ LysMCre$^{+/-}$Apoe$^{-/-}$), an $\alpha 9^{fl/fl}$ Apoe$^{-/-}$ mouse was crossed with a LysMCre$^{+/-}$Apoe$^{-/-}$ mouse. Littermates $\alpha 9^{fl/fl}$LysMCre$^{-/-}$ and $\alpha 9^{fl/fl}$LysMCre$^{-/-}$Apoe$^{-/-}$ mice were used as controls. Fn-EDA$^{+/+}$Apoe$^{-/-}$ mice constitutively expressing fibronectin containing an alternative spliced form (Fn-EDA) have been described previously. (Dhanesha N, Ahmad A, Prakash P, Doddapattar P, Lentz S R and Chauhan A K. Genetic Ablation of Extra Domain A of Fibronectin in Hypercholesterolemic Mice Improves Stroke Outcome by Reducing Thrombo-Inflammation. *Circulation.* 2015; 132:2237-47.) Aged mice (66-weeks old males) were procured from the Jackson laboratory. All the mice used in the present study were on the C57BL/6J background, and whenever possible, littermate control mice were used. Mice were genotyped by PCR according to protocols from the Jackson laboratory and as described previously. (Dhanesha N, Ahmad A, Prakash P, Doddapattar P, Lentz S R and Chauhan A K. Genetic Ablation of Extra Domain A of Fibronectin in Hypercholesterolemic Mice Improves Stroke Outcome by Reducing Thrombo-Inflammation. *Circulation.* 2015; 132:2237-47.) Mice were kept in standard animal house conditions with controlled temperature and humidity and had ad libitum access to standard chow diet and water. Both male and female mice (approximately 10-14 weeks) weighing 20-26 grams were utilized. The University of Iowa Animal Care and Use Committee approved all the procedures and studies were performed according to the current Animal Research: Reporting of In Vivo Experiment guidelines.

Quantitative Reverse Transcription (RT) Polymerase Chain Reaction (PCR)

WT mice were subjected brain ischemia/reperfusion injury by transiently occluding the right middle cerebral artery 60 minutes. Peripheral blood neutrophils were isolated (3, 6- and 24-hours post-reperfusion) using density gradient centrifuge as described previously. Total RNA from the neutrophils was isolated using the RNeasy mini kit (Qiagen). Total RNA (~400 ng) was reverse-transcribed using iScript™ Reverse Transcription Reagent Kit (BIORAD). PCR amplification of the cDNA (100 ng) was performed with the Applied Biosystems 7900HT Fast Real-Time PCR machine (total volume 20 μl) at the University of Iowa Genomics Division. Cycling conditions were 50° C. for 2 minutes, 95° C. for 10 minutes, and 40 cycles of 95° C. for 15 seconds and 60° C. for 1 minute. Data were analyzed using the comparative threshold cycle (ΔΔCT) method with values normalized to GAPDH. Primers for integrin α9 (sense: 5'-AAAGGCTGCAGCTGTCCCA-CATGGACGAAG-3' (SEQ ID NO:3) and antisense 5'-TTTAGAGAGATATTCTTCACAGCCCCCAAA-3' (SEQ ID NO:4)) GAPDH (sense: 5'-ACCACAGTC-CATGCCATCAC-3' (SEQ ID NO:5) and antisense and 5'-TCCACCACCCTGTTGCTGTA-3' (SEQ ID NO:6)) were used.

Neutrophil Adhesion and Transmigration Assay

Neutrophil adhesion and transmigration assays were performed under static condition using mouse brain endothelial cells ([BEND3], ATCC® CRL2299™). These assays were performed between passages 4 to 9. On the day of experiment, endothelial cell monolayers were treated with TNFα (100 ng/mL, R&D systems) for 3 hours. Peripheral neutrophils were isolated 3 hours after ischemia/reperfusion injury using density gradient centrifugation. For adhesion assay, neutrophils ($6\times10^5$) were labeled with calcein blue, AM (3 µM, Thermo Fisher Scientific) and added on the activated endothelial monolayer. Pre-wash and post-wash images were taken using Nikon Eclipse Ti-U inverted fluorescent microscope equipped with a 20×/0.8 Plan Apo lens, cooled CCD camera and a Nis Elements imaging software (Nikon). ImageJ software (NIH ImageJ, USA) was used for all the quantifications. For transmigration assay, BEND3 cells were cultured on 6.5-mm Transwells with 5-µm-pore-size polycarbonate membrane inserts (Costar). Aliquots of 200 ml labeled neutrophils ($6\times10^5$) were placed in the upper chamber, and cells were allowed to migrate at 37° C. to the lower chamber containing fMLP (10 µM, Sigma) for 16 hours. Neutrophils were counted using ADVIA 120 Hematology System. The representative image for each group was selected based upon the mean value.

Filament Stroke Model

Focal cerebral ischemia was induced by transiently occluding the right middle cerebral artery for 30 or 60 minutes. All the surgeries were performed by the person blinded to the experimental groups. Mice were anesthetized with isoflurane (1-1.5%) mixed with medical air. After midline incision, the right common carotid artery was temporarily ligated, and a filament (6.0 siliconized filament from Doccol Corp.) was inserted from the external carotid artery and advanced into the internal carotid artery up to the origin of the middle cerebral artery.

Reperfusion was achieved by removing the filament after 30 or 60 minutes and opening the common carotid artery. Throughout the surgery, the body temperature of the mice was maintained at 37° C.±1.0 using a heating pad. Buprenorphine (0.1 mg/kg, SC) was administered as an analgesic agent at every 6-12 hours for 48 hours post-surgery. Laser Doppler flowmetry (Perimed Instruments) was used for each mouse to confirm the successful induction of ischemia and reperfusion. Animals having more than 70% reduction in the regional cerebral blood flow (rCBF) and successful reperfusion (rCBF returns to 80-120% of baseline) were included in the study. The representative image for each group was selected based upon the mean value.

Embolic Stroke Model

Embolic stroke model was performed. Briefly, autologous embolus clot was prepared using arterial blood, supplemented with human fibrinogen (2 mg/ml, Sigma) and immediately clotted in a PE-50 tube for four hours at room temperature, followed by storage at 4° C. overnight. On the following day, 20 mm clot was washed in PBS by several passages from a PE-10 tube and transferred to a modified PE-10 catheter. Animals were anesthetized with 1-1.5% isoflurane during the surgery. The catheter containing a single 20 mm fibrin-rich clot was then introduced into the external carotid artery and advanced to the internal carotid artery. After the embolization, the catheter was removed, and the external carotid artery was blocked by cauterization. Laser Doppler flow monitoring was used to confirm the induction of ischemia. Throughout the surgery, the body temperature of the mice was maintained at 37±1.0° C. using a heating pad. The right jugular vein was cannulated for the administration of rtPA (Cathflo from Genentech, 10 mg/kg, 10% volume by bolus and remaining slow infusion for 30 minutes, 60 minutes post embolization). Buprenorphine (0.1 mg/kg, SC) was administered as an analgesic agent at every 6-12 hours for 48 hours post-surgery. The representative image for each group was selected based upon the mean value.

MRI Imaging, Infarct and BBB Breakdown Quantification

MRI was performed on day-1 post-ischemia/reperfusion. Briefly, animals were anesthetized with isoflurane (2.5% induction, 1.2% maintenance) and placed in the bore of the 7.0 Tesla Mill (Agilent Technologies Inc.) with a two-channel receive-only surface coil. Following scout scans, high-resolution images were acquired with a 9-minute T2-weighted 2D fast spin-echo sequence oriented coronally. Imaging parameters included TR/TE=6380 ms/83 ms, echo train length of 12, and 7 signal averages to achieve voxel resolution 0.10 mm×0.10 mm×0.50 mm with no gaps. For the quantification of BBB breakdown, this was followed by intraperitoneal injection of gadobuterol (Gadavist, Bayer HealthCare) at a dose of 0.3 mmol/kg and subsequent multiple 3D gradient echo acquisitions in the same coronal plane (TR/TE=25/3 ms, flip angle 30°, resolution 0.1 mm×0.1 mm×0.25 mm, 3 minutes per scan) acquired over 25 minutes. Total imaging time for each animal was approximately 25 minutes. The area of infarction was quantified by the person blinded to the experimental groups, using NIH Image J software by outlining the zone with abnormally hyperintense regions in each brain slice, and the total infarct volume was obtained by summation of the infarcted areas multiplied by the slice thickness. The corrected total infarct volume (%) was calculated as follows to correct for brain swelling due to edema after ischemia. Corrected infarct volume (%)=[volume of contralateral hemisphere−(volume of ipsilateral hemisphere−volume of infarct)]/Volume of contralateral hemisphere×100. For quantification of infarcts 1-hour after ischemia and just before the reperfusion, apparent diffusion coefficient (ADC) maps were generated from trace images from a diffusion-weighted multi-shot echo-planar pulse sequence using an 8-shot readout. An image matrix of 128×128 was acquired over a 25 mm×25 mm field of view with 0.5 mm slices. Acquisition parameters included TR/TE=8000 ms/23.3 ms, 6 diffusion directions with b=2000 s/mm2 and two images with b=0 for a total scan time of 8 minutes 48 seconds.

Functional Assessment of Neurological Outcome:

All the functional assessment of neurological outcome was performed by a person blinded to the experimental groups. Bederson Scale: The Bederson scale is a global neurological assessment that was developed to measure neurological impairments following stroke. Neurological outcomes were assessed by an observer blinded to the experimental groups and was scored on a four-point scale: 0, no observable neurological deficit (normal); 1, failure to extend left forepaw on lifting the whole body by tail (mild); 2, circling to the contralateral side but normal posture at rest (moderate); 3, leaning to the contralateral side at rest (severe); 4, no spontaneous motor activity. Modified Neurological Severity Score (mNSS): The mNSS rates neurological functioning with a minimum neurological score of 3, and maximum of 18 (higher score indicates a better outcome). The mNSS includes a composite score of six different tests, which are: spontaneous activity, symmetry in the movement of four limbs, forepaw outstretching, climbing, body proprioception and responses to vibrissae touch, as previously mentioned. We evaluated mNSS on day-1, day-3, and day-7, post-stroke. Cylinder test: The cylinder test was used to assess forelimb use and rotation asymmetry. Mice were placed in a clear cylinder videotaped for 5 minutes. Forelimb use of the first contact against the wall after rearing and during lateral exploration was analyzed. The final score= (nonimpaired forelimb movement−impaired forelimb movement)/(nonimpaired forelimb movement+impaired forelimb movement+both movement). On day-1 and day-3 post-stroke, we could not detect much vertical exploration, and hence we analyzed data only for day-7. Accelerated rotarod test: The accelerated rotarod (Harvard Apparatus) was used to access post-stroke motor coordination. For this, mice were trained for 3-5 days on rotarod rotating at 4 RPM such that animals may walk forward to keep balance. Training is considered complete when mice can stay on the rod rotating at 4 RPM for at least 1 minute. On the test day, mice were placed on the rod rotating at 4 RPM and then rotation was set in acceleration mode (4-40 RPM in 5 minutes). Latency to fall was recorded for each mouse on day-1, day-3, and day-7, post-stroke. Adhesive tape removal test: The Adhesive Removal test evaluates long term functional sensory-motor deficit after ischemia/reperfusion injury. During the test, a small adhesive patch (rectangular 0.3×0.4 cm) was applied to each forepaw. Immediately after the placement of patches both forelimbs were pressed simultaneously to minimize bias. The mouse was then placed in transparent Perspex box for 120 seconds, and the time to contact (mouth sensitivity) and remove (correct dexterity) each adhesive tape is recorded.

Ipsilateral Edema Quantification

Ipsilateral hemisphere edema, the volumes of both hemispheres were calculated in arbitrary units (pixels) from the sum of Mill coronal slice areas using Image J software. Edema area was expressed as a percentage of the normal areas in the contralateral, unaffected hemisphere. The extent of swelling was calculated using the equation: Extent of edema=(volume of ipsilateral hemisphere−volume of contralateral hemisphere)/volume of contralateral hemisphere× 100.

Laser Speckle Contrast Imaging

To assess post-reperfusion cerebral blood flow, we used a laser speckle contrast imager (moorFLPI-2 from Moor instruments), which provides real-time, high-resolution blood flow images. Briefly, mice were anesthetized using isoflurane (2.5% induction, 1% maintenance) and incision was made to provide access to the skull. Mineral oil was applied to avoid dryness. Speckle imaging was obtained using a temporal filter (250 frames, 10 sec/frame) at 0.1 Hz at baseline, after middle cerebral artery occlusion, and 5, 20, 40, and 60 minutes post-reperfusion. Blood fluxes were measured in the middle cerebral artery supplied region and fluxes were expressed in arbitrary units using a 12-color palette. The representative image for each group was selected based upon the mean value.

Bone Marrow Transplantation

Bone marrow transplantation (BMT) were performed at 7-8 weeks of age. All mice were on the C57BL/6J background. Recipient mice were irradiated with 2 doses of 6.5-Gy at an interval of 4 hours between the first and second irradiations. Under sterile conditions, bone marrow cells were extracted from excised femurs and tibias of euthanized donor mice. Bone marrow cells ($1\times10^7$) were suspended in sterile PBS and injected into the retro-orbital venous plexus of lethally irradiated recipient mice. After transplantation, mice were maintained in sterile cages and fed autoclaved food and water ad libitum. We performed four different sets of BMT experiments: 1) irradiated aged-WT mice reconstituted with BM from α9fl/fl donors ($α9^{fl/fl}$ BM→WT mice), 2) irradiated aged-WT mice reconstituted with BM from $α9^{fl/fl}$ LysMcre$^{+/-}$ donors ($α9^{fl/fl}$ LysMcre$^{+/-}$BM→WT mice), 3) irradiated Fn-EDA$^{+/+}$Apoe$^{-/-}$ mice reconstituted with BM from LysMcre$^{+/-}$Apoe$^{-/-}$ donors (LysMcre$^{+/-}$ Apoe$^{-/-}$−BM→Fn-EDA$^{+/+}$Apoe$^{-/-}$ mice), and 4) irradiated Fn-EDA$^{+/+}$Apoe$^{-/-}$ mice reconstituted with BM from α9 LysMcre$^{+/-}$Apoe$^{-/-}$ donors ($α9^{fl/fl}$ LysMcre$^{+/-}$Apoe$^{-/-}$− BM→Fn-EDA$^{+/+}$Apoe$^{-/-}$ mice). BMT success was analyzed after 4 weeks by PCR to check presence of the genomic DNA (of the respective donor mice) in peripheral blood mononuclear cells from transplanted mice (not shown). Complete blood counts were obtained using automated veterinary hematology analyzer (ADVIA) to ascertain that BMT did not affect the number of BM-derived blood cells.

Immunofluorescence

Immunostaining was performed in paraffin embedded sections from brain (23 hours post-reperfusion) and isolated peripheral neutrophils. All sections were subjected to heat-induced antigen retrieval. Sections were blocked with 5% normal goat serum in Tris-buffered saline at room temperature (RT). Brain sections were washed thrice with PBS for 5 minutes and incubated overnight with primary antibodies for platelet (rat anti-mouse CD41; Bio-rad), anti-fibrin (ogen) (1:400, Acris Antibodies) at 4° C. Isolated neutrophils were incubated overnight with Integrin α9 (1:100, Santa Cruz Biotechnologies Inc.) at 4° C. After washing, sections were labelled with appropriate secondary antibodies [goat anti-rabbit IgG Alexa flour-546 (1:400, Invitrogen), goat anti-mouse IgG Alexa flour-546 (1:400, Invitrogen), and goat anti-rat IgG Alexa flour-488 (1:400, Invitrogen)]. Nuclei were stained using DAPI. Isotype-matched immunoglobulins were used as a negative control. Images were taken using Nikon Eclipse Ti-U inverted fluorescent microscope equipped with a 40×/0.75 and 20×/0.8 Plan Apo lens, cooled CCD camera and a Nis Elements imaging software (Nikon). ImageJ software (NIH ImageJ, USA) was used for all the quantifications. Number of total and occluded vessels in brain sections was counted by the person blinded to the experimental groups. The thrombotic index was calculated by dividing occluded vessels from a total number of vessels. The representative image for each group was selected based upon the mean value.

Immunohistochemistry

Brain cortical sections (obtained after 23 hours of reperfusion) were deparaffinized, rehydrated, and subjected to heat-induced antigen retrieval. Briefly, sections were blocked with 5% serum at room temperature (RT), from the species in which the secondary antibody was raised. Endogenous peroxidase activity was quenched with 0.1% hydrogen peroxide in methanol for 15 min. Sections were stained with primary antibodies for neutrophil (rat anti-mouse Ly6B.2; 1:100; Bio-rad), in the presence of 5% rabbit serum. After overnight incubation at 4° C., slides were washed with PBS for 5 minutes and incubated with biotinylated secondary antibody for 1 hour at RT. Slides were then incubated with streptavidin-HRP for 40 minutes at RT, washed and incubated with DAB substrate until color develops. Slides were then washed and counter-stained with hematoxylin, mounted using an aqueous mounting medium and examined under a light microscope (Olympus). Incubation without primary antibodies and with isotype-matched immunoglobulins was used as a negative control for immunostaining. Quantification: In four different regions of the infarct and surrounding area extravascular neutrophils (400× magnification) were quantified by counting the immunoreactive cells (brown color staining). NIH Image J software (with the plugin for individual cell analysis) was used for neutrophil quantification. Each data represents a mean of 16 fields from 4 serial sections (separated by 30 µm). The representative image for each group was selected based upon the mean value.

Fluoro-Jade C Staining

For Fluoro-Jade-C staining, deparaffinized brain sections were stained in 0.001% Fluoro-Jade C (Sigma, catalog #AG325) in 0.1% acetic acid for 20 min. Slides were subsequently washed 3 times in ultrapure water for 2 min each and dried at room temperature. Dried slides were cleared in xylene and coverslips were mounted using Permount. Nuclei were stained using DAPI. Images were taken using Nikon Eclipse Ti-U inverted fluorescent microscope equipped with a 40×/0.75 and 20×/0.8 Plan Apo lens, cooled CCD camera and a Nis Elements imaging software (Nikon). For quantification, Fluoro-Jade-C positive cells were counted in two different regions of the infarct and surrounding area for each mouse. NIH Image J software (with the plugin for individual cell analysis) was used for the quantification. The representative image for each group was selected based upon the mean value.

Western Blot

Brain cortical tissue was collected (23 hours post-reperfusion) from the infarcted and surrounding areas and homogenized in RIPA buffer (25 mM Tris pH 7.4, 150 mM NaCl, 1% NP-40) containing 0.1% SDS and 4% protease inhibitor (complete protease inhibitor cocktail, Roche, catalog #11836153001). Samples were sonicated for total 30 seconds with 10 seconds gap. Tissue lysates were centrifuged at 14000×g for 20 min at 4° C. and supernatants were used for the determination of protein content (by Lowry method) and subsequent Western blot analysis. Total lysates were mixed with sample loading buffer (Novex by Life Technologies, catalog #NP0007) and heated at 95° C. for 5 min. 20 µg of total protein was loaded per well, electrophoresed and transferred to a polyvinylidene difluoride (PVDF) membrane. After blocking for 60 min with blocking buffer (5% nonfat dry milk, 50 mM Tris-HCl pH 7.5, 0.05% Tween-20), membranes were incubated with: anti-fibrin (ogen) (1:5000, Acris Antibodies), phospho-NF-κB p65 (Ser536) (1:1000, Cell Signaling Technologies), NF-κB p65 (1:1000, Cell Signaling Technologies) and anti-CD41 (1:1000, GeneTex) at 4° C. overnight, followed by appropriate secondary antibodies (polyclonal goat anti-rabbit IgG, Dako) conjugated to horseradish peroxidase (HRP). Enhanced chemiluminescence kit (Thermo Scientific) was used for Western blots. All blots were stripped and reanalyzed for the β-actin (anti-beta actin antibody from Abcam) as a loading control. The intensity of the bands was measured by densitometry and quantified using NIH-Image J software.

ELISA Assay for TNF-α and IL-1β

After 23 hours of reperfusion, cortical brain tissue was collected from the infarcted and surrounding areas and lysed in tissue lysis buffer (20 mM Tris-Cl, pH 8.0, 10 mM NaCl, 2% Triton X-100). Supernatants from brain homogenates were used for determination of tumor necrosis factor-α (TNF-α) and interleukin-1β (IL-1β) with commercially available mouse ELISA kits (TNF-α, IL-1β, both from R&D Systems) according to the manufacturer's instructions.

Cyclosporine A Treatment $\alpha 9^{fl/fl}$Apoe$^{-/-}$ and $\alpha 9^{fl/fl}$LysMCre$^{+/-}$Apoe$^{-/-}$ mice were treated for 7 consecutive days with a low intraperitoneal non-toxic dose of cyclosporine A (Sigma, 30024-25; 10 mg/kg/day for 3 days followed by 5 mg/kg/day for 4 days), before performing the stroke surgery and the treatment was continued up to day-7 of the reperfusion.

Treatment with Anti-Integrin α9 Antibody

Mice were randomly assigned and infused with either anti-α9 antibody (55A2C, 200 µg/mouse, provided by Gene Techno Science Co., Ltd, Japan) or with control Ig isotype (200 µg/mouse, Rockland antibodies and assays) intravenously, 75 minutes after the induction of ischemia.

Neutrophil Extracellular Traps Assay

For neutrophil extracellular trap assay, bone-marrow derived neutrophils were isolated from both genotypes. For immunofluorescence microscopy, $2 \times 10^5$ neutrophils were stimulated with PMA (20 ng/mL) and seeded onto coverslips coated with 0.001% poly-L-lysine (Sigma) and fixed with 4% paraformaldehyde. Next, neutrophils were then permeabilized with 0.1% Triton-X100 for 15 min at room temperature. Blocking was with 1% bovine serum albumin. The primary antibody was anti-Histone H3 antibody (Abcam 61251, diluted 1:100), and the FITC-conjugated secondary antibody was from SouthernBiotech (4052-02, diluted 1:250). DNA was stained with Hoechst 33342 (Invitrogen). he representative image for each group was selected based upon the mean value.

Statistical Analysis

Results are reported as mean±SEM except for the neurological scores (Bederson score and mNSS), and sensorimotor test (cylinder test, accelerated rotarod test and adhesive removal test) where median±range was used. The number of experimental animals in each group was based on power calculations for the primary parameter (infarct volume) with mean differences and standard deviations taken from pilot data at power 80% with an alpha of 0.05. For statistical analysis, GraphPad Prism software, version 7.04 was used. Shapiro-Wilk test was used to check normality, and Bartlett's test was used to check equal variance. The statistical significance was assessed using either unpaired t-test or one-way ANOVA followed by Holm-Sidak's or Fisher's LSD multiple comparisons test (for normally distributed data) and Mann Whitney test or Kruskal-Wallis tests followed by Dunn's multiple comparisons test (for not normally distributed data). P<0.05 was considered to be statistically significant.

Results

Integrin α9-Deficient Neutrophils Exhibit Reduced Adhesion and Trans-Endothelial Migration Evidence from clinical studies suggest rapid changes in gene expression profile in peripheral neutrophils after ischemic stroke. To determine if integrin α9 expression on peripheral neutrophils changes after acute ischemic stroke, neutrophils were isolated from the wild-type (WT) mice after 1 hour of ischemia followed by 3, 6, and 24 hours of post-ischemia/reperfusion (FIG. 1A). Littermate mice with sham surgery were used as controls. Integrin α9 expression was observed to be significantly up-regulated following 3 and 6 hours of reperfusion, but not at 24 hours (FIG. 1B). These results were confirmed in parallel by flow cytometry (FIG. 1C). Given the early postnatal mortality in global $\alpha 9^{-/-}$ mice due to respiratory failure, we generated myeloid-specific integrin α9$^{-/-}$ (α9$^{fl/fl}$ LysMcre$^{+/-}$) mice (FIG. 8). Western blot and immunofluorescence analysis confirmed the lack of integrin α9 on neutrophils isolated from the bone marrow (BM) of α9$^{fl/fl}$LysMcre$^{+/-}$ mice (FIGS. 1D and 1E). Previously, it was shown that global deletion of α9 in mice results in a defect in granulopoiesis. In contrast, we found that complete blood counts (CBCs) were comparable between α9$^{fl/fl}$LysMCre$^{+/-}$ and α9$^{fl/fl}$ mice (Table 1), suggesting that myeloid-specific deletion of α9 does not result in impaired granulopoiesis and these mutant mice could be used as a genetic model to determine the role of integrin α9 in ischemic stroke.

TABLE 1

Table 1: Complete blood counts from 8-10 weeks old mice were obtained using automated veterinary hematology analyzer (Advia).

|  | α9$^{fl/fl}$ | α9$^{fl/fl}$LysMCre$^{+/-}$ |
| --- | --- | --- |
| WBC (10$^3$/μL) | 13.3 ± 1.0 | 12.2 ± 0.4 |
| RBC (10$^6$/μL) | 9.9 ± 0.2 | 9.8 ± 0.1 |
| HGB (g/dL) | 15.9 ± 0.1 | 15.8 ± 0.2 |
| HCT (%) | 46.4 ± 0.7 | 45.7 ± 0.5 |
| PLT (10$^3$/μL) | 931 ± 48 | 930 ± 36 |
| Neutrophil (10$^3$/μL) | 0.5 ± 0.1 | 0.5 ± 0.1 |
| Monocytes (10$^3$/μL) | 1.5 ± 0.3 | 1.8 ± 0.3 |

Value are expressed as mean ± SEM, n = 4, 5.
P = Non-significant versus control α9$^{fl/fl}$ mice.

Having observed elevated integrin α9 expression on peripheral neutrophil after acute ischemic stroke, we determined whether integrin α9-deficiency inhibits post-stroke peripheral neutrophil adhesion and trans-endothelial migration. Peripheral neutrophils were isolated after 1 hour of ischemia and 3 hours of reperfusion and assayed for adhesion to TNF (tumor necrosis factor)-α activated mouse brain endothelial cells. We found that neutrophils from the α9$^{fl/fl}$LysMCre$^{+/-}$ mice exhibited reduced adhesion and transendothelial migration, compared to α9fl/fl littermate mice (FIGS. 1F and 1G). Together, these results suggest that poststroke neutrophil integrin α9 is upregulated and contributes to adhesion and transendothelial migration.

Myeloid-Specific α9$^{-/-}$ Mice Exhibit Improved Stroke Outcome

Figure 10:
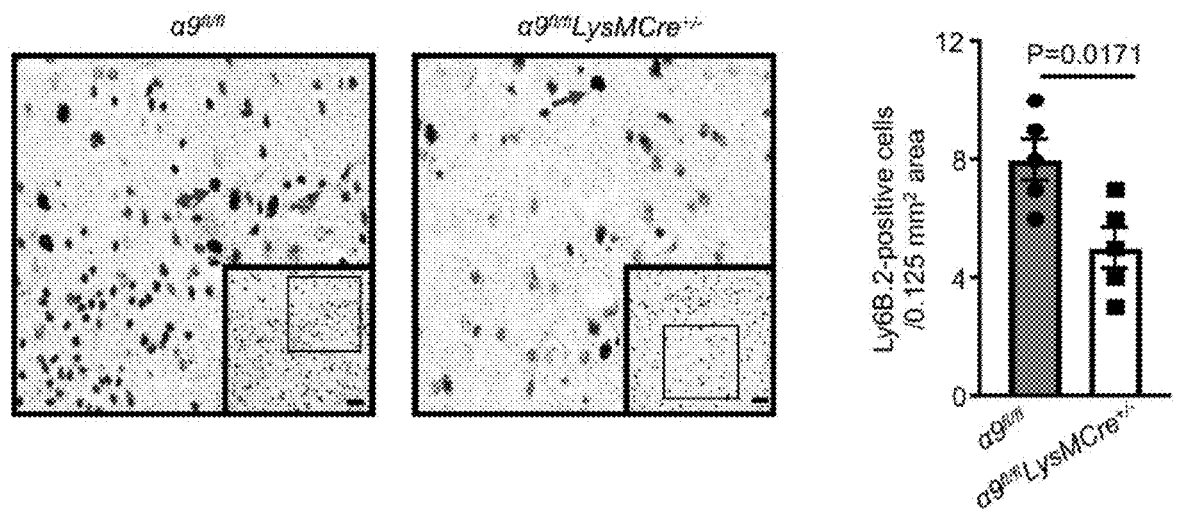
FIG. 10: Reduced neutrophil infiltration in myeloid-cell specific α9−/− mice on WT background. Left: Representative immunostained images for neutrophils (brown Ly6B.2-positive cells indicated by red arrows). Boxed region (lower magnification). Inset in the boxed region is magnified and shown in the microphotograph. Scale bar: 100 µm. Right: Quantification. Data are mean±SEM, n=5/group. Statistical analysis: unpaired t-test.
Figures 11A, 11B:
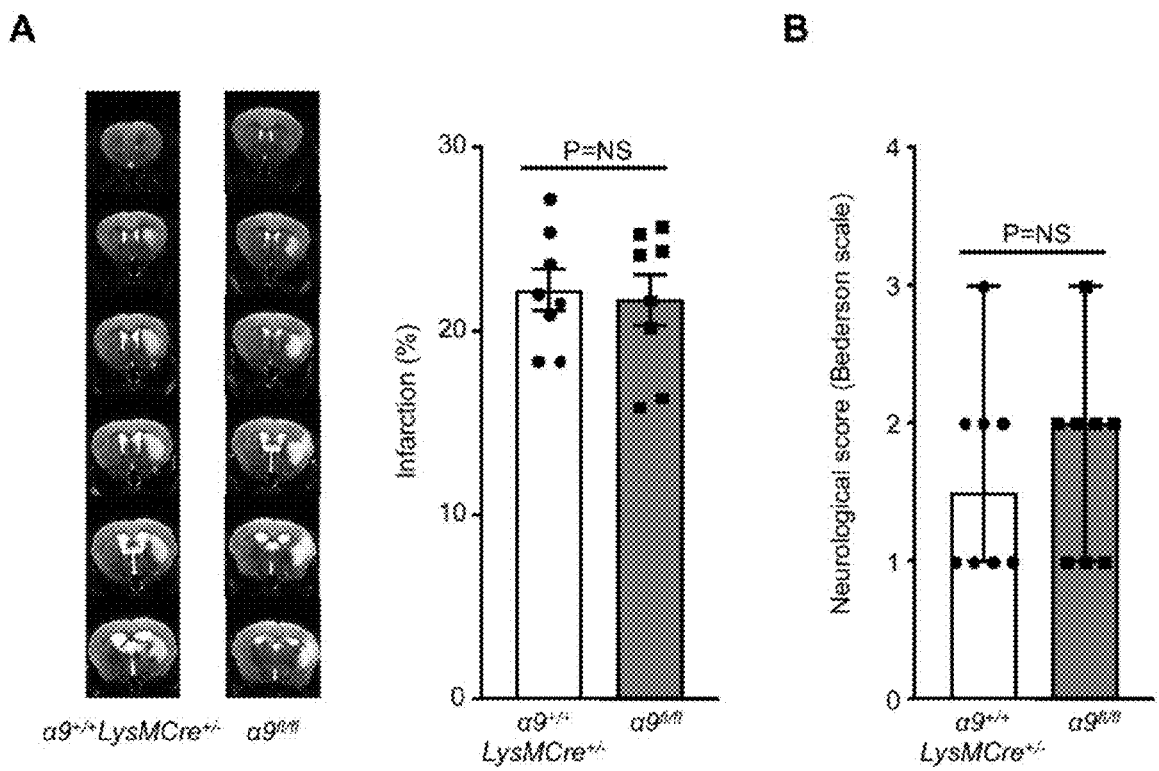
FIGS. 11A-11B: α9fl/fl and α9+/+LysMCre+/− mice exhibit comparable stroke outcome. A. Left: Representative MRI from one mouse of each genotype on day-1. White is the infarct area. Right: Corrected mean infarct area of each genotype (N=8/group). B. Neurological outcome (Bederson score) from each genotype as assessed before sacrifice on day 1 (depicted as scatter plots, including median). Data are mean±SEM, n=8/group. Statistical analysis: unpaired t-test (A), Mann Whitney test (B).
Figure 12:
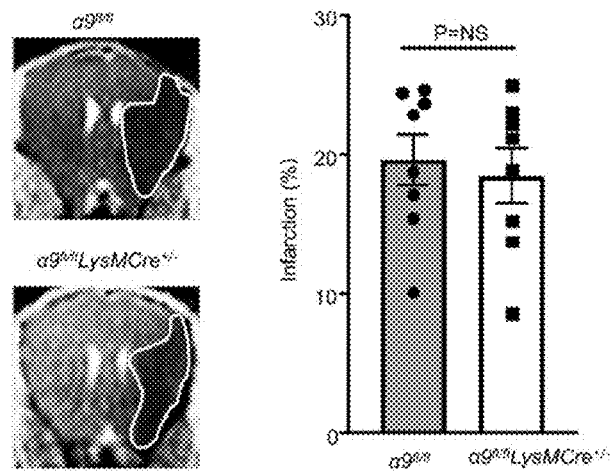
FIG. 12. α9fl/fl and α9fl/flLysMCre+/− mice exhibit comparable infarct volume when quantified 1 hour after ischemia. Left: Representative MRI from 1 mouse of each genotype on day 1. Black is the infarct area. Right: Corrected mean infarct area of each genotype. Data are mean±SEM (n=8/group). Statistical analysis: unpaired t-test.

Next, we determined stroke outcomes in α9$^{fl/fl}$ and α9$^{fl/fl}$LysMcre$^{+/-}$ mice on WT background subjected to 1 hour of ischemia and 23 hours of reperfusion in the filament model. Both male and female α9$^{fl/fl}$LysMCre$^{+/-}$ mice exhibited smaller infarcts and better neurological outcome on day 1 when compared with α9fl/fl mice (FIGS. 9A-9D), concomitant with reduced neutrophil infiltration in the infarcted brain (FIG. 10). Infarcts and neurological scores were comparable between α9fl/fl and α9$^{+/+}$LysMCre$^{+/-}$ mice, thus ruling out nonspecific effects of LysM-Cre recombinase expression (FIG. 11A-11B) on stroke outcome. To determine whether integrin α9 deficiency on myeloid cells also protects during the ischemic phase, we quantified infarcts just before reperfusion. Infarcts were comparable between α9fl/fl and α9$^{fl/fl}$LysMCre$^{+/-}$ mice subjected to 1 hour of ischemia (FIG. 12). Together these results suggest that lack of integrin α9 on myeloid cells improves stroke outcome only in the setting of ischemia/reperfusion injury.

Based on this compelling phenotype, and according to updated STAIR recommendations, we next determined stroke outcome in mice with preexisting comorbidity, hyperlipidemia, which is known to exacerbate ischemic damage by promoting endothelial injury, inflammation, oxidative stress, and neuronal death. We generated α9$^{fl/fl}$LysMCre$^{+/-}$ mice on the hyperlipidemic apolipoprotein E-deficient (Apoe$^{-/-}$) background. All the mice were fed a normal chow diet after weaning until 8-10 weeks, an age at which no significant vascular lesions are found (not shown), to minimize the potential confounding effects of advanced atherosclerotic lesions, which can impair collateral flow and indirectly influence the stroke outcome. Bodyweight, plasma cholesterol, triglycerides, and complete blood counts were comparable between these groups (Tables 2 and 3).

TABLE 2

Table 2. Total plasma cholesterol, plasma triglycerides concentrations were measured from each mouse using enzymatic colorimetric assays according to the manufacturers' instructions.

|  | α9$^{fl/fl}$ Apoe$^{-/-}$ | α9$^{fl/fl}$LysMcre$^{+/-}$ Apoe$^{-/-}$ |
| --- | --- | --- |
| Plasma total cholesterol (mg/dL) | 225.6 ± 10.1 | 230.5 ± 13.2 |
| Plasma Triglycerides (mg/dL) | 49.2 ± 4.1 | 48.1 ± 4.9 |
| Body weight (g) | 24.1 ± 0.6 | 24.4 ± 0.7 |

Values are expressed as mean ± SEM, n = 5, 6.
P = Non-significant versus control α9$^{fl/fl}$Apoe$^{-/-}$ mice.

TABLE 3

Table 3: Complete blood counts from 8-10 weeks old mice were obtained using automated veterinary hematology analyzer (Advia).

|  | α9$^{fl/fl}$ Apoe$^{-/-}$ | α9$^{fl/fl}$LysMcre$^{+/-}$ Apoe$^{-/-}$ |
| --- | --- | --- |
| WBC (10$^3$/μL) | 13.5 ± 1.1 | 13.2 ± 0.2 |
| RBC (10$^6$/μL) | 10 ± 0.1 | 10.8 ± 0.2 |
| HGB (g/dL) | 14.7 ± 0.1 | 15.3 ± 0.3 |
| HCT (%) | 47.8 ± 0.3 | 49.3 ± 1.1 |
| PLT (10$^3$/μL) | 1268 ± 16 | 1288 ± 47 |
| Neutrophil (10$^3$/μL) | 0.3 ± 0.1 | 0.3 ± 0.1 |
| Monocytes (10$^3$/μL) | 2.2 ± 0.3 | 2.0 ± 0.3 |

Value are expressed as mean ± SEM, n = 5, 6.
P = Non-significant versus control α9$^{fl/fl}$Apoe$^{-/-}$ mice.

Figures 13A, 13B:
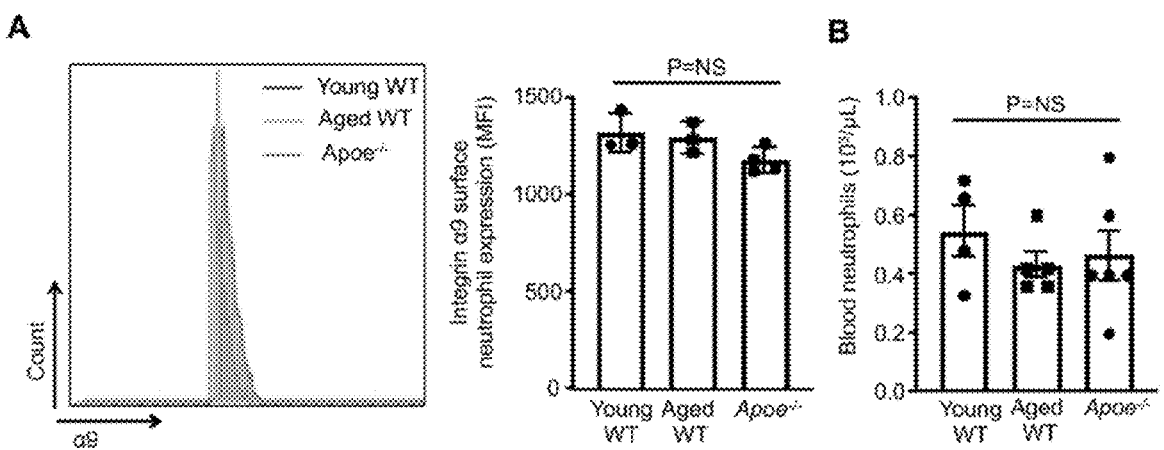
FIGS. 13A and 13B. Integrin α9 surface expression levels on neutrophils and blood neutrophils count. A. Left: Representative image of flow-cytometric analysis for each group. Right: Quantification of α9 expression in peripheral neutrophils, n=3/group. B. Blood neutrophil count from each group obtained using automated veterinary hematology analyzer (Advia). Value are expressed as mean±SEM, n=4, 5, 6. Statistical analysis: 1-way ANOVA followed by Fisher's LSD multiple comparisons test.
Figure 14:
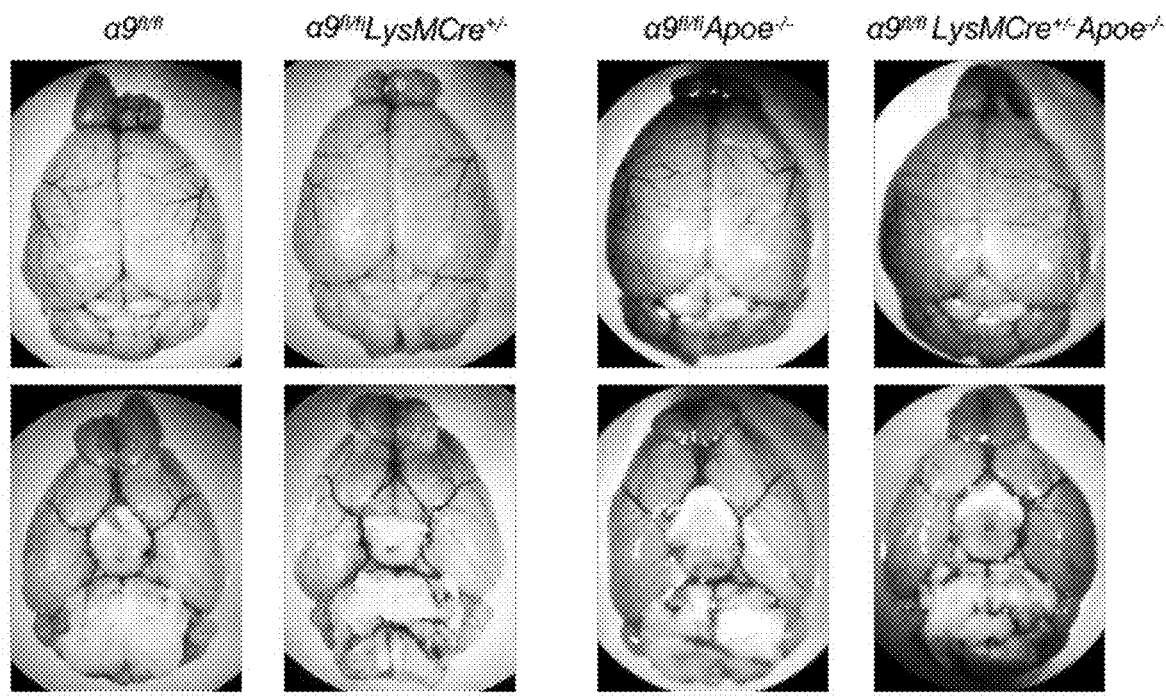
FIG. 14. Comparison of cerebrovascular anatomy. Anesthetized mice were given an intracardiac injection of India ink and were then exsanguinated according to approved animal protocol. Circle of Willis and bilateral posterior communicating arteries was comparable among groups indicating there was no strain-related differences in gross cerebrovascular anatomy.

Neutrophil count and surface expression levels of integrin α9 were comparable between WT and Apoe$^{-/-}$ mice, suggesting that hyperlipidemia does not modulate integrin α9 expression on neutrophils (FIG. 13). To ensure rigor and confirm that the observed effect is generalizable in a broader context, susceptibility to ischemia/reperfusion injury was evaluated in the same mouse following 1, 3, and 7 days of reperfusion in two models of stroke: the filament model and the embolic model (FIG. 2A). α9$^{fl/fl}$LysMCre$^{+/-}$Apoe$^{-/-}$ mice exhibited smaller infarcts (~32%) and better neurological outcomes at day 1 when compared with α9$^{fl/fl}$Apoe$^{-/-}$ mice (FIGS. 2B and 2C) in both male and female mice. Consistent with these results, at day 7, α9$^{fl/fl}$ LysMCre$^{+/-}$Apoe$^{-/-}$ mice showed a better survival rate (~70%) compared to α9$^{fl/fl}$ Apoe$^{-/-}$ mice (~35%, P=0.04; FIG. 2D). Next, using the same mouse, we evaluated the modified Neurological Severity Score (mNSS) that rates neurological function based on spontaneous activity, symmetry in limb movement, forepaw outstretching, climbing, body proprioception, and responses to vibrissae touch (on the scale of 3-18; higher score indicates a better outcome). α9$^{fl/fl}$LysMcre$^{+/-}$Apoe$^{-/-}$ mice demonstrated significantly improved neurological outcomes on days 1, 3, day 7 when compared to α9$^{fl/fl}$ Apoe$^{-/-}$ mice (FIG. 2E). Consistent with these results, α9$^{fl/fl}$LysMCre$^{+/-}$ Apoe$^{-/-}$ mice exhibited smaller infarcts, a better survival rate and improved neurological outcomes in the embolic model reperfused with tPA (FIGS. 2F through 2I). Laser Doppler flow measurements (Table 4) and physiological parameters (Table 5) were similar among groups before, during, and after ischemia. Moreover, no gross differences in cerebrovascular anatomy were observed between groups (FIG. 14A-14B).

TABLE 4

Table 4: Laser Doppler Flowmetry (LDF) was similar among groups during and after ischemia.

| | $\alpha 9^{fl/fl}$ Apoe$^{-/-}$ | $\alpha 9^{fl/fl}$LysMcre$^{+/-}$ Apoe$^{-/-}$ |
|---|---|---|
| Ischemia LDF (% of baseline) | 19.9 ± 2.2 | 20.6 ± 2.7 |
| Reperfusion LDF (% of baseline) | 94.3 ± 8.9 | 93.3 ± 5.6 |

Values are expressed as mean ± SEM, n = 4, 5.
P = Non-significant versus control $\alpha 9^{fl/fl}$Apoe$^{-/-}$ mice.

TABLE 5

Table 5. Physiological parameters were similar among groups during the procedure.

| | Before ischemia | | | After 60 min ischemia | | |
|---|---|---|---|---|---|---|
| | PO$_2$ mm Hg | PCO$_2$ mm Hg | pH | PO$_2$ mm Hg | PCO$_2$ mm Hg | pH |
| $\alpha 9^{fl/fl}$Apoe$^{-/-}$ | 101.1 ± 20.9 | 44.6 ± 5.3 | 7.42 ± 0.05 | 93.8 ± 22.9 | 69.5 ± 20.8 | 7.31 ± 0.04 |
| $\alpha 9^{fl/fl}$LysMcre$^{+/-}$ Apoe$^{-/-}$ | 83.8 ± 16.1 | 64.5 ± 11.9 | 7.39 ± 0.05 | 91.7 ± 20.9 | 79.5 ± 23.4 | 7.31 ± 0.06 |

Values are expressed as mean ± SEM, n = 5 mice/group.
P = Non-significant versus control $\alpha 9^{fl/fl}$Apoe$^{-/-}$ mice.

Figure 15:
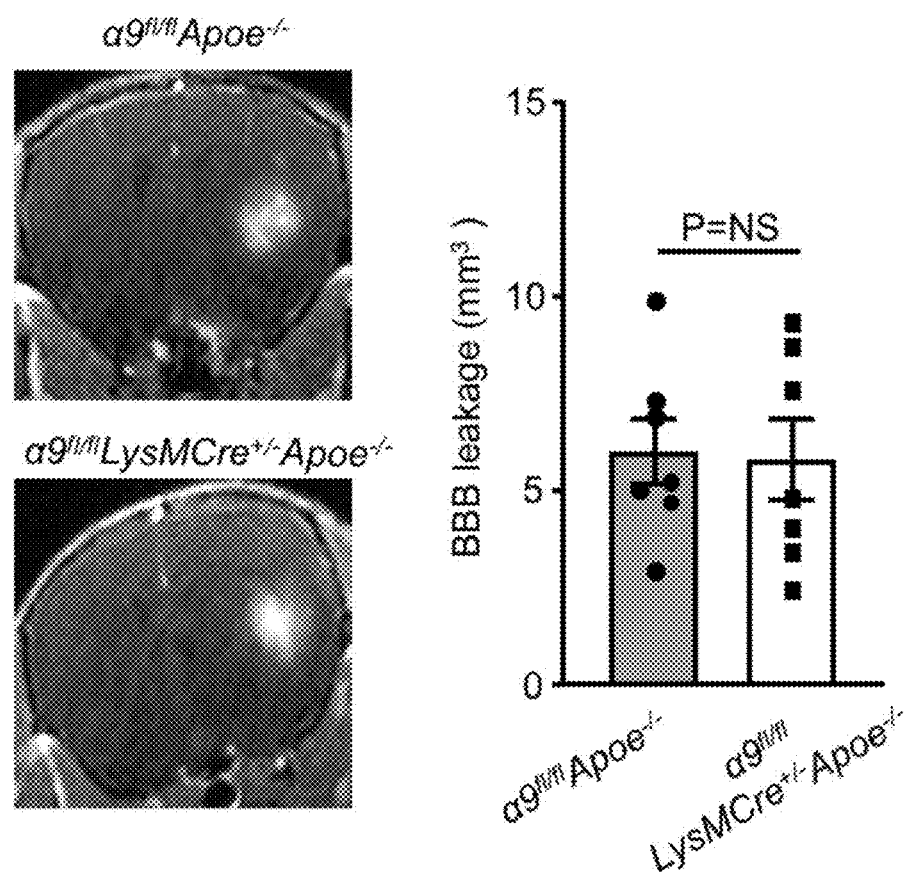
FIG. 15. BBB breakdown was comparable between α9fl/flApoe−/− and α9fl/flLysMCre+/−Apoe−/− mice. BBB breakdown was quantified on day-1 after ischemia (1-hour)/reperfusion injury using gadobuterol (Gadavist, Bayer HealthCare) at a dose of 0.3 mmol/kg and subsequent multiple 3D gradient echo acquisitions in MRI. Left: Representative MRI from 1 mouse of each genotype on day 1. White area indicates BBB breakdown. Right: BBB breakdown area of each genotype. Data are mean±SEM, n=7/group. Statistical analysis: unpaired t-test.
Figures 16A, 16B, 16C, 16D:
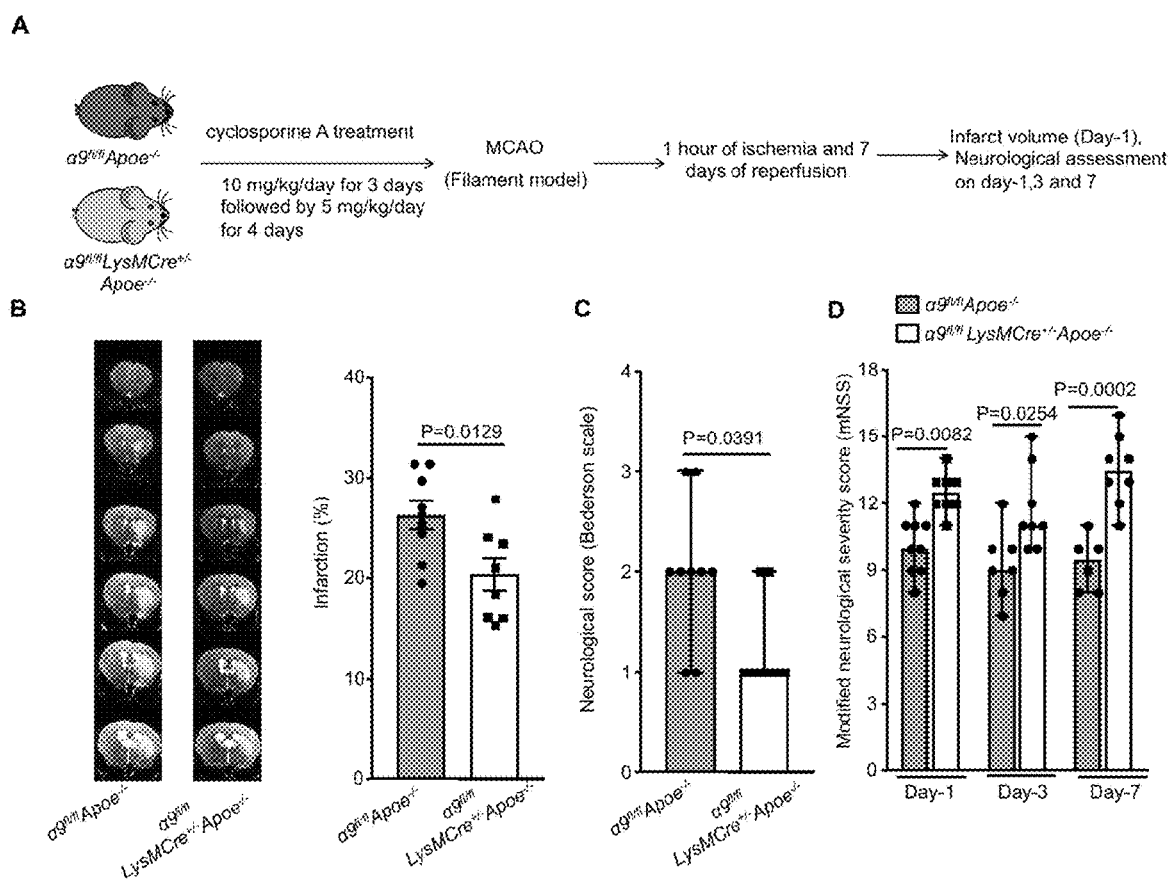
FIGS. 16A-16D. Cyclosporin A treated α9fl/flLysMCre+/−Apoe−/− mice exhibited reduced infarct volume and improved neurological outcome compared to cyclosporin A treated α9fl/flApoe−/− mice. A. Schematic of experimental design. B. Left: Representative MRI from 1 mouse of each genotype on day 1. White is the infarct area. Right: Corrected mean infarct area of each genotype, n=9, 8. C. Neurological outcome (Bederson score) from each genotype as assessed before sacrifice on day 1 (depicted as scatter plots, including median, n=9, 8). D. Modified Neurological Severity Score (mNSS) at day 1, 3, and 7 based on spontaneous activity, symmetry in the movement of 4 limbs, forepaw outstretching, climbing, body proprioception and responses to vibrissae touch. Higher score indicates a better outcome, n=9, 8, 7, 8, 6, 8. Data are mean±SEM (B), median±range (C and D). Statistical analysis: unpaired t-test (B), Mann Whitney test (C), Kruskal-Wallis test followed by Fisher's LSD multiple comparisons test (D).
Figures 17A, 17B, 17C, 17D:
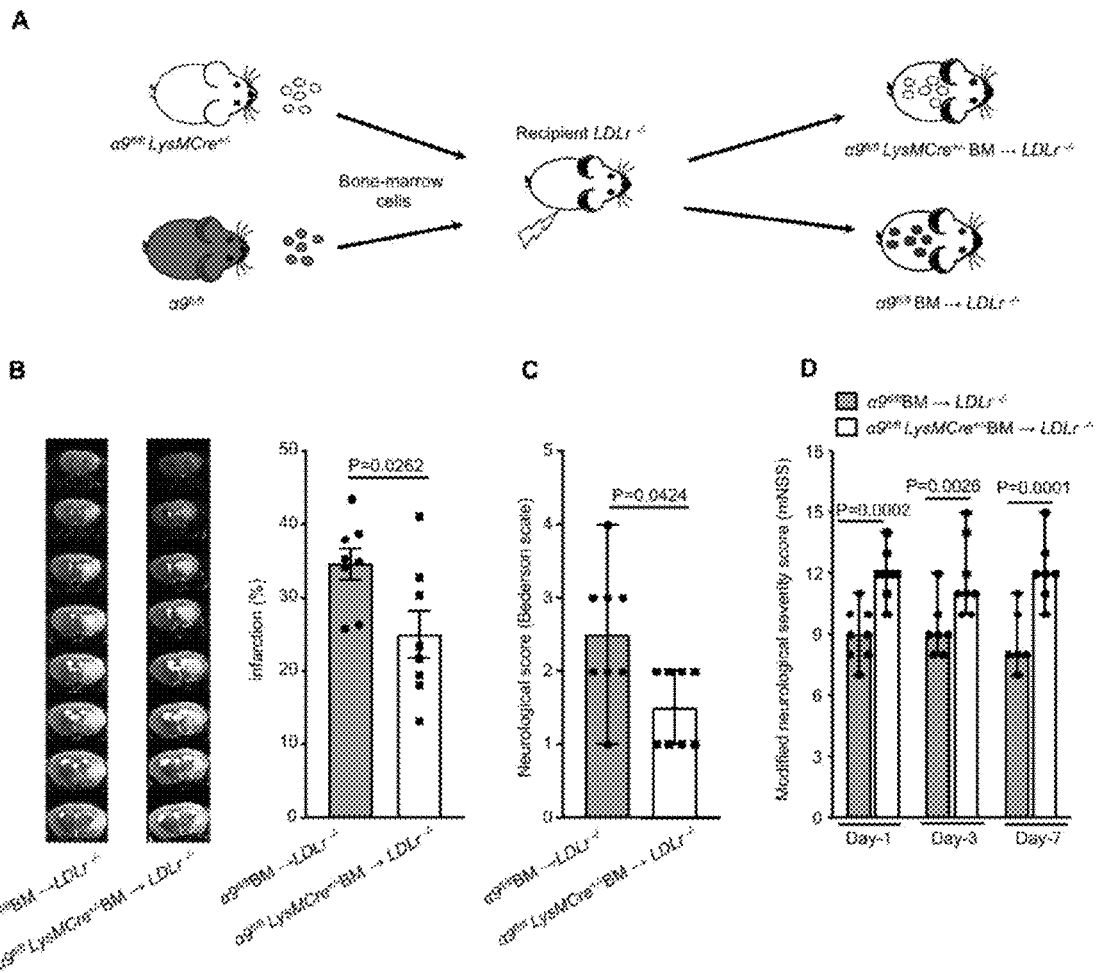
FIGS. 17A-17D. Irradiated LDLr−/− mice transplanted with bone-marrow of α9fl/fl LysMCre+/− mice exhibit improved stroke outcome. A. Schematic of experimental design. B. Left: Representative MRI from 1 mouse of each genotype on day 1. White is the infarct area. Right: Corrected mean infarct area of each genotype (n=8/group). C. Neurological outcome (Bederson score) from each genotype as assessed before sacrifice on day 1 (depicted as scatter plots, including median, n=8/group). D. Modified Neurological Severity Score (mNSS) at day 1, 3, and 7 based on spontaneous activity, symmetry in the movement of 4 limbs, forepaw outstretching, climbing, body proprioception and responses to vibrissae touch. Higher score indicates a better outcome, n=8, 8, 7, 8, 6, 7. Data are mean±SEM (B), median±range (C and D). Statistical analysis: unpaired t-test (B), Mann Whitney test (C), Kruskal-Wallis test followed by Fisher's LSD multiple comparisons test (D).
Figure 18:
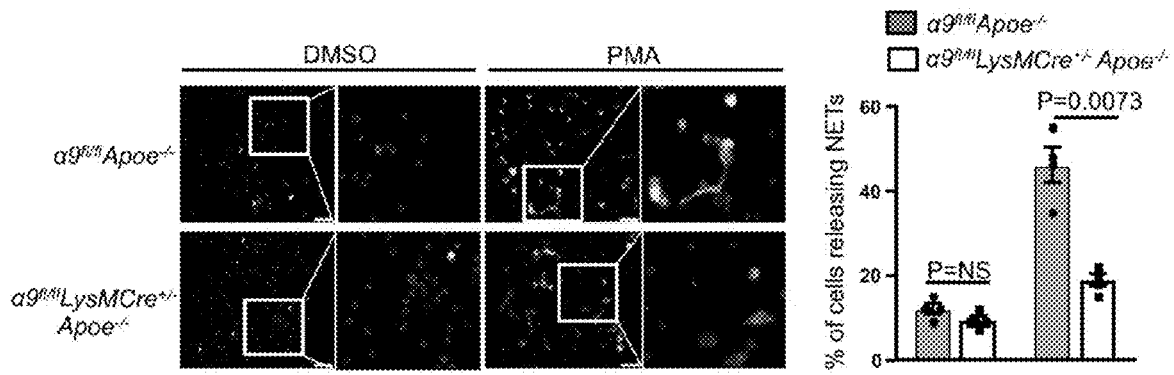
FIG. 18. Neutrophils from the α9fl/flLysMCre+/−Apoe−/− mice display decreased NETosis. Left panels show representative microphotographs of neutrophil extracellular traps (NETs) with anti-histone H3 (citrulline R2+R8+R17, red), and nuclei (Hoechst, blue). Scale bar: 50 Right panel shows quantification of percentage of cells releasing NETs. Data are mean±SEM, n=4/group. Statistical analysis: unpaired t-test.
Figures 19A, 19B, 19C, 19D, 19E:
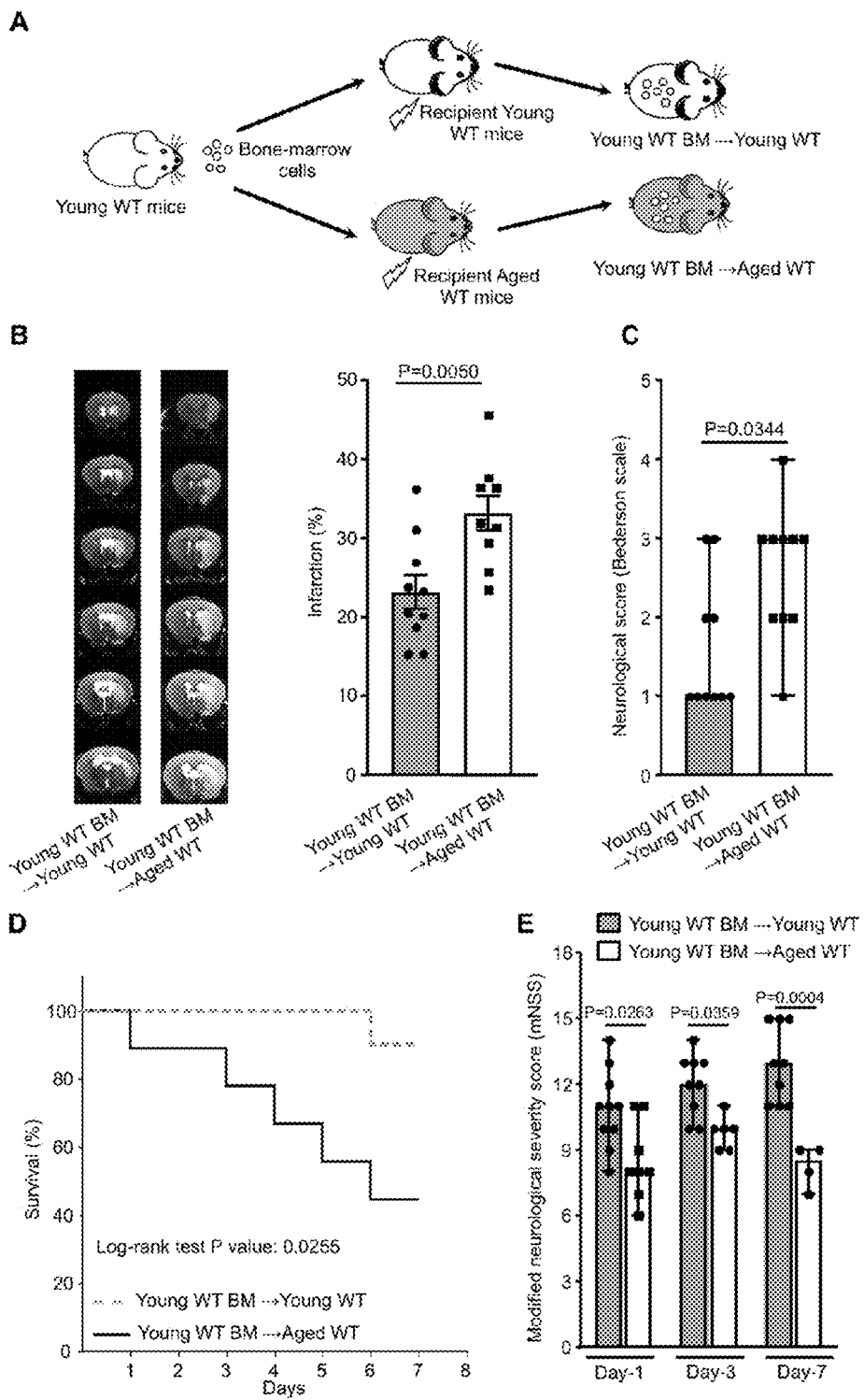
FIGS. 19A-19E. Irradiated aged WT mice transplanted with BM of young WT mice exhibit worsen stroke outcome. A. Schematic of experimental design. B. Left: Representative magnetic resonance imaging from one mouse of each genotype on day 1 in filament model. White is the infarct area. Right: Corrected mean infarct volumes of each genotype (n=10, 9). C. Neurological outcome (Bederson score) from each genotype as assessed on day 1 (higher score indicates worse outcome, n=10, 9). D. Survival rate between day 0 to day 7 after 60 min transient ischemia in filament model. E. Modified Neurological Severity Score (mNSS) at days 1, 3, and 7 in filament model based on spontaneous activity, symmetry in the movement of 4 limbs, forepaw outstretching, climbing, body proprioception and responses to vibrissae touch (higher score indicates a better outcome, n=10, 8, 9, 6, 9, 4). Data are mean±SEM (B) and median±range (C and E). Statistical analysis: unpaired t-test (B), Mann-Whitney test (C), Comparison of survival curves was evaluated by log-rank (Mantel-Cox) test (D), Kruskal-Wallis test followed by Fisher's LSD multiple comparisons test (E).

Lack of Apoe in mice promotes blood-brain barrier breakdown and neuronal death by activating the proinflammatory cyclophilin A-NF-κB (nuclear factor-κB)-matrix metalloproteinase 9 pathway in pericytes. Since blocking cyclophilin A with cyclosporin A reverses excessive blood-brain barrier breakdown and neuronal death in Apoe$^{-/-}$ mice, we pretreated $\alpha 9^{fl/fl}$LysMCre$^{+/-}$Apoe$^{-/-}$ and $\alpha 9^{fl/fl}$Apoe$^{-/-}$ mice with cyclosporin A and determined the protective effect of integrin α9 deficiency on stroke outcome, independent of blood-brain barrier breakdown. At baseline, blood-brain barrier leakage was comparable between $\alpha 9^{fl/fl}$Apoe$^{-/-}$ and $\alpha 9^{fl/fl}$LysMCre$^{+/-}$Apoe$^{-/-}$ mice (FIG. 15). Cyclosporin A treated $\alpha 9^{fl/fl}$LysMCre$^{+/-}$Apoe$^{-/-}$ mice exhibited reduced infarct size and improved neurological outcome compared with cyclosporin A treated $\alpha 9^{fl/fl}$Apoe$^{-/-}$ mice (FIG. 16). Furthermore, α9 deficiency on myeloid cells significantly reduced infarct volume and improved neurological outcomes in another model of hyperlipidemia, low-density lipoprotein receptor-deficient mice (FIGS. 17A-17D). Together these results suggest that lack of α9 on myeloid cells improve stroke outcomes in the setting of hyperlipidemia.

Figures 3A, 3B, 3C, 3D:
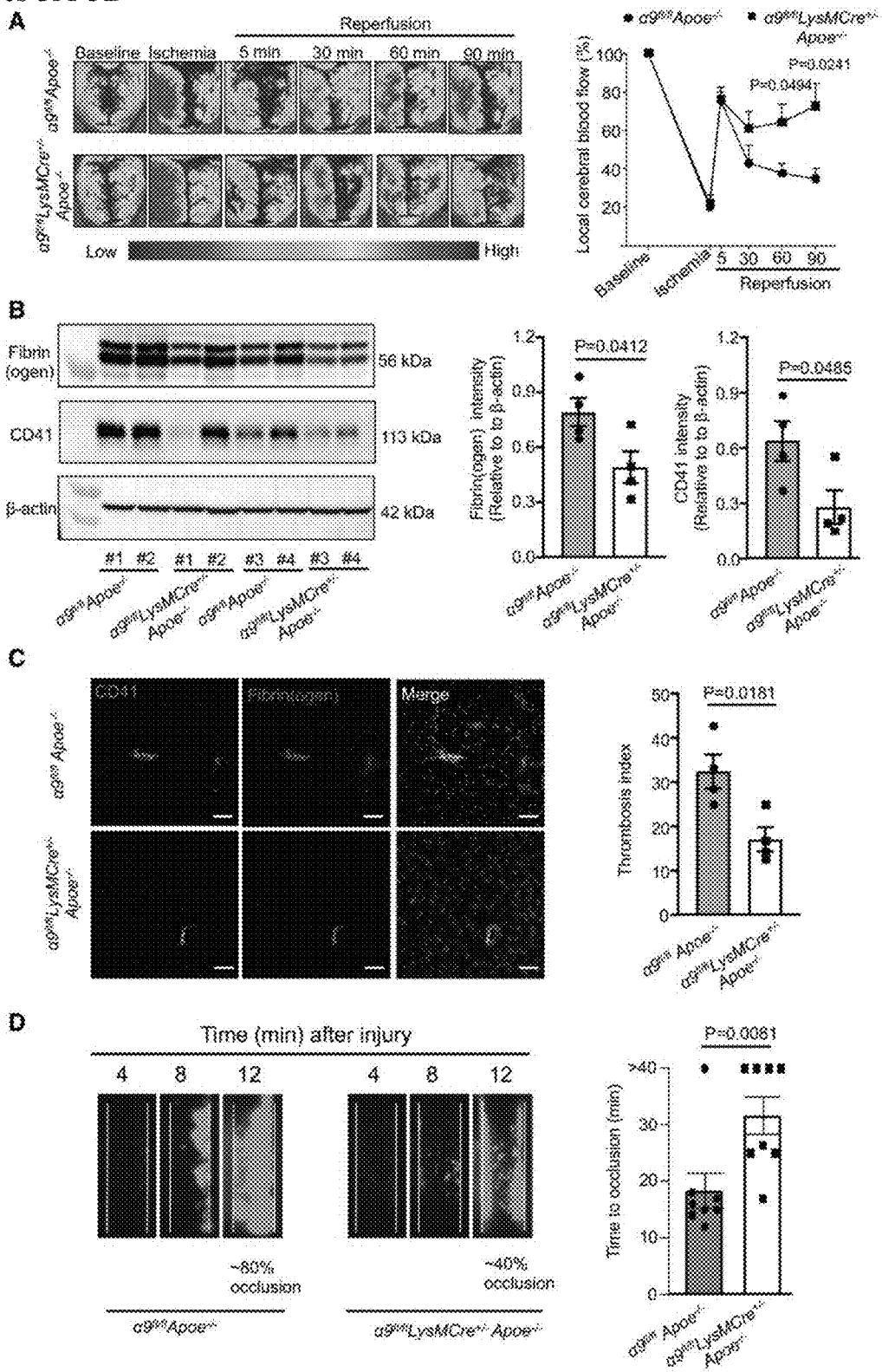
FIGS. 3A-3D. Deletion of integrin α9 in myeloid cells improves local cerebral blood flow and inhibits post-ischemia/reperfusion thrombosis. A. Left: Representative images were taken using laser speckle imaging of regional cerebral blood flow (CBF) in the cortical region. Right: Quantification at different time points (5-90 minutes). n=6 and 5. B. Brain homogenates from the infarcted and peri-infarcted area following 1-hour ischemia/23 hours reperfusion were processed for Western blotting: Representative Western blots and densitometric analysis of fibrin(ogen) and platelets (CD4-positive). β-Actin was used as a loading control. n=4 mice/group. C. Left: Representative immunostaining images for platelet (CD41-positive, green) and fibrin (ogen) (red). Right: Thrombotic index, n=4/group. D. Left: Representative microphotographs depicting percentage occlusion ~12 minutes after $FeCl_3$-injured carotid arteries as visualized by upright intravital microscopy. Platelets were labeled with calcein green. White lines delineate the arteries. Right: Mean time to complete occlusion of $FeCl_3$-injured carotid artery, n=8 and 8. Data are mean±SEM. Statistical analysis: 2-way ANOVA followed by Holm-Sidak multiple comparisons test (A), unpaired t-test (B, C D, and D). MCAO indicates middle cerebral artery occlusion.

Myeloid-Specific α9$^{-/-}$ Mice Exhibited Improved Local Cerebral Blood Flow and Reduced Post-Ischemia/Reperfusion Thromboinflammation Both thrombosis and inflammation are known to contribute to the pathophysiology of ischemic stroke. To determine whether improved stroke outcome in the $\alpha 9^{fl/fl}$LysMCre$^{+/-}$Apoe$^{-/-}$ mice was associated with reduced post-ischemia/reperfusion cerebral thrombosis and improved local cerebral blood flow, laser speckle imaging was performed at different time points. We found that regional cerebral blood flow was improved at 60 and 90 minutes following reperfusion in $\alpha 9^{fl/fl}$ LysMCre$^{+/-}$Apoe$^{-/-}$ mice (FIG. 3A). Consistent with these results, we observed significantly reduced intracerebral fibrin(ogen) and platelet (CD41-positive) deposition and thrombotic index in the $\alpha 9^{fl/fl}$LysMCre$^{+/-}$Apoe$^{-/-}$ mice when compared with $\alpha 9^{fl/fl}$ Apoe$^{-/-}$ mice, FIGS. 3B and 3C). These results led us to hypothesize that, following reperfusion, integrin α9 may promote thrombosis and thereby exacerbate stroke outcome. To test this hypothesis, aged-matched male mice (same age that was used for stroke evolution) were subjected to experimental thrombosis (FeCl$_3$ injury-induced carotid artery thrombosis). Using intravital microscopy, we found that $\alpha 9^{fl/fl}$ LysMCre$^{+/-}$ Apoe$^{-/-}$ mice developed smaller thrombi (~40% occlusion) when compared to $\alpha 9^{fl/fl}$ Apoe$^{-/-}$ mice (~80% occlusion), 12 minutes after FeCl$_3$ injury-induced thrombosis (FIG. 3D). The mean time to complete occlusion was significantly prolonged in the $\alpha 9^{fl/fl}$LysMCre$^{+/-}$Apoe$^{-/-}$ mice (FIG. 3D) suggesting that integrin α9 contributes to arterial thrombosis.

Figures 4A, 4B, 4C, 4D, 4E, 4F:
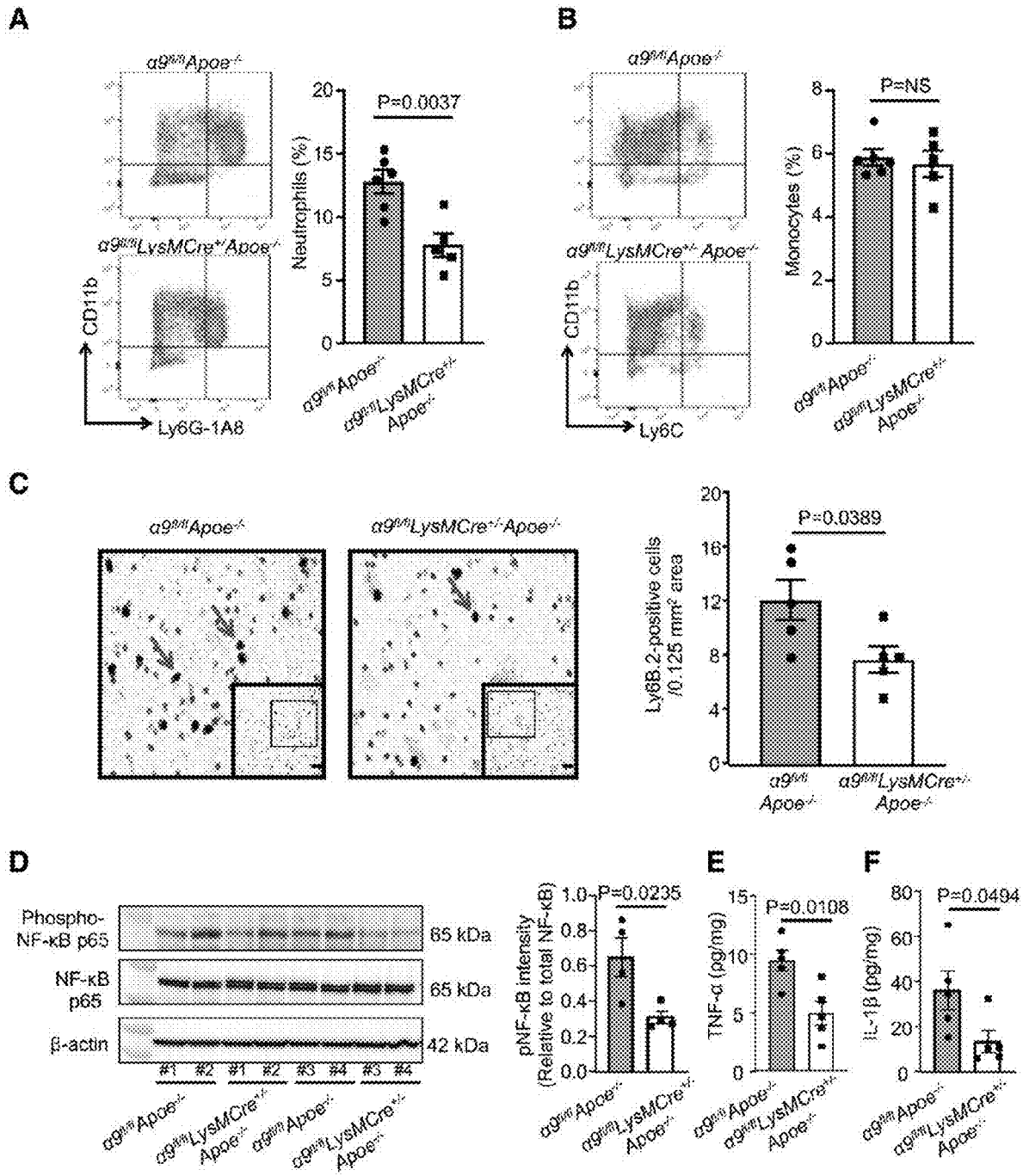

To determine if improved stroke outcome in the $\alpha 9^{fl/fl}$LysMCre$^{+/-}$Apoe$^{-/-}$ mice was associated with reduced post-ischemia/reperfusion cerebral inflammation, neutrophil and monocyte influx was measured within the infarct and peri-infarct regions of the perfused brain after 1 hour of ischemia and 23 hours of reperfusion in the filament model. Using flow cytometry, we found a significant reduction in neutrophil influx in the $\alpha 9^{fl/fl}$LysMCre$^{+/-}$Apoe$^{-/-}$ mice, while monocyte influx was unaltered in brain homogenates prepared from the infarct and peri-infarct regions when compared with $\alpha 9^{fl/fl}$Apoe$^{-/-}$ mice (FIGS. 4A and 4B). In parallel, we confirmed these results using immunohistochemistry and found significantly reduced neutrophil influx (Ly6B.2-positive cells) in the $\alpha 9^{fl/fl}$LysMCre$^{+/-}$Apoe$^{-/-}$ mice when compared with $\alpha 9^{fl/fl}$Apoe$^{-/-}$ mice (FIG. 4C). Total leukocyte counts were similar among genotypes (Table 3). The neutrophil influx was absent in the non-ischemic region of the contralateral hemisphere or in sham-operated mice (not shown). In alignment with these results, we found a significant reduction in the inflammatory markers such as phospho-NF-κB p65, TNF-α and IL (interleukin)-1β in brain homogenates prepared from the infarcted and surrounding areas of $\alpha 9^{fl/fl}$LysMcre$^{+/-}$Apoe$^{-/-}$ mice when compared with $\alpha 9^{fl/fl}$Apoe$^{-/-}$ mice (FIGS. 4D through 4F). Furthermore, we found a reduction in neuronal injury (Fluro-Jade C-positive) and ipsilateral edema in the $\alpha 9^{fl/fl}$LysMCre$^{+/-}$Apoe$^{-/-}$ mice when compared with $\alpha 9^{fl/fl}$Apoe$^{-/-}$ mice (FIGS. 4G and 4H). To determine whether integrin α9 modulates neutrophils extracellular traps formation and thereby exacerbates cerebral thromboinflammation, we performed neutrophil extracellular trap assay in vitro using stimuli phorbol 12-myristate 13-acetate.

The percentage of cells releasing neutrophil extracellular traps was significantly reduced in α9$^{fl/fl}$LysMCre$^{+/-}$Apoe neutrophils stimulated with phorbol 12-myristate 13-acetate (FIG. 18A-18D). Together, these results suggest that myeloid-specific integrin α9 exacerbates stroke outcome by promoting post-ischemia/reperfusion thromboinflammation.

Myeloid-Specific Integrin α9 Exacerbates Adverse Stroke Outcome Partially Through its Ligand Extracellular Matrix Protein Fn-EDA The extracellular matrix protein Fn-EDA (fibronectin containing extra domain A) is an endogenous ligand for integrin α9β1 that is known to mediate cell adhesion and migration. We have previously reported that Fn-EDA$^{+/+}$ mice exhibit worse stroke outcomes when compared to WT mice. To evaluate whether myeloid-specific integrin α9 aggravates adverse stroke outcome through Fn-EDA, we transplanted irradiated Fn-EDA$^{+/+}$Apoe$^{-/-}$ mice with BM from either α9$^{fl/fl}$LysMcre$^{+/-}$Apoe$^{-/-}$ or α9$^{fl/fl}$Apoe$^{-/-}$ mice (FIG. 5A). The efficiency of BM transplant procedure was checked by genotyping 4-weeks after the procedure. Complete blood counts were comparable, suggesting that BMT did not affect the number of BM-derived blood cells (Table 6).

Figures 6A, 6B, 6C, 6D, 6E, 6F, 6G:
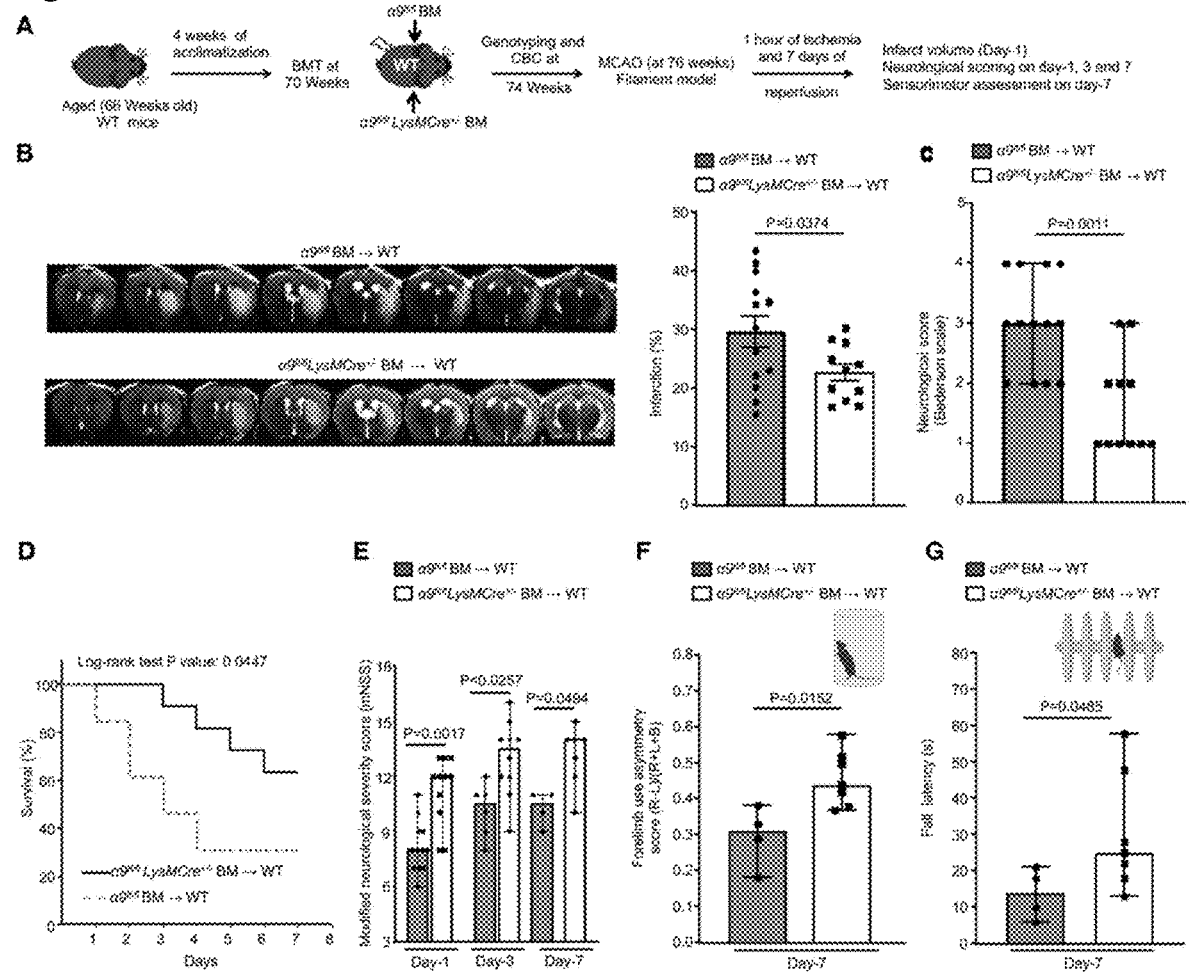
FIGS. 6A-6G: Deletion of integrin α9 on myeloid cells improves stroke outcome and enhances the sensorimotor recovery in aged mice. A, Schematic of experimental design. B, Left: Representative magnetic resonance imaging from 1 mouse of each group on day 1. White is the infarct area. Right: Corrected mean infarct volumes of each genotype (n=13 and 11). C, Neurological outcome (Bederson score) from each genotype as assessed on day 1 (higher score indicates a worse outcome, n=13 and 11). D, The survival rate after 60 min transient ischemia. E, Modified neurological severity score (mNSS) at days 1, 3, and 7 based on spontaneous activity, symmetry in the movement of 4 limbs, forepaw outstretching, climbing, body proprioception, and responses to vibrissae touch (higher score indicates a better outcome, n=13, 11, 6, 10, 4, and 7). F, Poststroke neurological, behavioral recovery as analyzed by cylinder test on day 7, n=4 and 7. G, Poststroke motor function as analyzed by accelerated rotarod on 7, n=4 and 7. Data are mean±SEM (B) and median±range (C and E-G). Statistical analysis: unpaired t test (B), Mann-Whitney test (C, F, and G) Comparison of survival curves was evaluated by log-rank (Mantel-Cox) test (D), Kruskal-Wallis test followed by Fisher LSD multiple comparisons test (E). MCAO indicates middle cerebral artery occlusion.

Aging is considered as one of the most important risk factors for acute ischemic stroke. To test the hypothesis that myeloid-specific integrin α9 exacerbates stroke outcome not only in young mice but also in aged mice, we transplanted irradiated 70-week-old aged mice mice reconstituted with WT-BM from either α9$^{fl/fl}$ LysMcre$^{+/-}$ or α9$^{fl/fl}$ mice (FIG. 6A). The success of the BM transplant procedure was confirmed by genotyping and measuring complete blood counts (Table 7).

TABLE 7

Table 7: Complete blood counts from chimeric aged mice were obtained using automated veterinary hematology analyzer (Advia).

|  | α9$^{fl/fl}$ BM➔ aged WT | α9$^{fl/fl}$ LysMcre$^{+/-}$BM➔ aged WT |
|---|---|---|
| WBC (10$^3$/μL) | 15.3 ± 1.3 | 15.6 ± 1.2 |
| RBC (10$^6$/μL) | 8.5 ± 0.1 | 8.6 ± 0.2 |
| HGB (g/dL) | 10.5 ± 0.3 | 10.5 ± 0.2 |
| HCT (%) | 41 ± 0.8 | 40.8 ± 0.8 |
| PLT (10$^3$/μL) | 1092 ± 57 | 1048 ± 43 |

TABLE 6

Table 6: Complete blood counts from 8-10 weeks old mice were obtained using automated veterinary hematology analyzer (Advia).

|  | α9$^{fl/fl}$ Apoe$^{-/-}$BM ➔ EDA$^{+/+}$Apoe$^{-/-}$ | α9$^{fl/fl}$ LysMcre$^{+/-}$Apoe$^{-/-}$ BM➔ EDA$^{+/+}$Apoe$^{-/-}$ | LysMCre$^{+/-}$ Apoe$^{-/-}$BM➔ EDA$^{+/+}$Apoe$^{-/-}$ | α9fl/fl LysMCre$^{+/-}$ Apoe$^{-/-}$BM➔ EDA$^{+/+}$Apoe$^{-/-}$ |
|---|---|---|---|---|
| WBC (10$^3$/μL) | 13 ± 0.5 | 12.7 ± 0.5 | 14.1 ± 1.2 | 13.7 ± 1.0 |
| RBC (10$^6$/μL) | 9.3 ± 0.3 | 8.8 ± 0.2 | 9.5 ± 0.14 | 9.8 ± 0.16 |
| HGB (g/dL) | 14.8 ± 0.5 | 13.8 ± 0.2 | 15 ± 0.3 | 15.7 ± 0.22 |
| HCT (%) | 44.6 ± 1.6 | 42.9 ± 0.6 | 46.4 ± 0.36 | 47.5 ± 0.92 |
| PLT (10$^3$/μL) | 917 ± 37 | 867 ± 42.9 | 828 ± 46 | 921 ± 19 |
| Neutrophil (10$^3$/μL) | 0.6 ± 0.1 | 0.4 ± 0.1 | 0.5 ± 0.1 | 0.4 ± 0.07 |
| Monocytes (10$^3$/μL) | 2.2 ± 0.1 | 2.4 ± 0.3 | 8.4 ± 0.95 | 8.2 ± 0.9 |

Value are expressed as mean ± SEM, n = 5/group.
P = Non-significant.

Susceptibility to ischemia/reperfusion injury was evaluated in the same mouse following 1, 3, and 7 days of reperfusion using the filament model. We found significantly reduced infarct volume in α9$^{fl/fl}$LysMcre$^{+/-}$Apoe$^{-/-}$-BM-F→EDA$^{+/+}$Apoe$^{-/-}$ mice when compared to α9$^{fl/fl}$Apoe$^{-/-}$-BMF→EDA$^{+/+}$Apoe$^{-/-}$ mice that was concomitant with improved neurological outcome and survival rate at day 1, 3 and 7 (FIGS. 5B through 5E). However, Fn-EDA$^{+/+}$Apoe$^{-/-}$ mice transplanted with BM of LysMCre$^{+/-}$Apoe$^{-/-}$ mice (LysMCre$^{+/-}$Apoe$^{-/-}$-BM→Fn-EDA$^{+/+}$Apoe$^{-/-}$) exhibited increased infarcts and worse neurological outcomes compared to Apoe$^{-/-}$ mice transplanted with BM of Lys MCre$^{+/-}$Apoe$^{-/-}$ mice (LysMCre$^{+/-}$Apoe$^{-/-}$-BM→Apoe$^{-/-}$, FIGS. 5B and 5C). We speculate that stroke exacerbation in Fn-EDA$^{+/+}$Apoe$^{-/-}$ mice (which constitutively express Fn-EDA) is due to elevated (3-fold increase) plasma Fn-EDA levels when compared to Apoe$^{-/-}$ mice. Together these results suggest that Fn-EDA partially contributes to α9-mediated stroke exacerbation.

Deficiency of Integrin α9 on Myeloid Cells Improves Stroke Outcome and Enhances the Sensorimotor Recovery in the Comorbid Condition of Aging TABLE 7-continued Table 7: Complete blood counts from chimeric aged mice were obtained using automated veterinary hematology analyzer (Advia).

|  | α9$^{fl/fl}$ BM➔ aged WT | α9$^{fl/fl}$ LysMcre$^{+/-}$BM➔ aged WT |
|---|---|---|
| Neutrophil (10$^3$/μL) | 0.7 ± 0.2 | 0.5 ± 0.1 |
| Monocytes (10$^3$/μL) | 7.7 ± 0.9 | 6.7 ± 0.9 |

Value are expressed as mean ± SEM, n = 6/group.
P = Non-significant.

Susceptibility to 60 minutes ischemia was evaluated on the same aged mice (76 weeks) following 1, 3, and 7 days of reperfusion in the filament model. We found significantly reduced infarct in the myeloid-specific integrin α9$^{-/-}$ aged WT mice that were concomitant with improved neurological outcomes and survival rate at day 1, 3 and 7 ($P<0.05$ vs. control aged WT mice; FIGS. 6B through 6E). In parallel, we evaluated post-stroke sensorimotor recovery in the same chimeric aged mice using the cylinder and accelerated rotarod tests. The cylinder test is a sensorimotor test to assess asymmetry in forelimb use during vertical exploratory behavior inside a glass cylinder, whereas the accelerated rotarod test evaluates motor coordination and balance. We found significantly enhanced sensorimotor recovery on day-7 in myeloid-specific integrin $\alpha 9^{-/-}$ aged WT mice compared to control (FIGS. 6F and 6G). We were not able to evaluate 28-day stroke outcomes in aged mice because of higher mortality observed in controls.

Figures 7A, 7B, 7C, 7D, 7E, 7F, 7G:
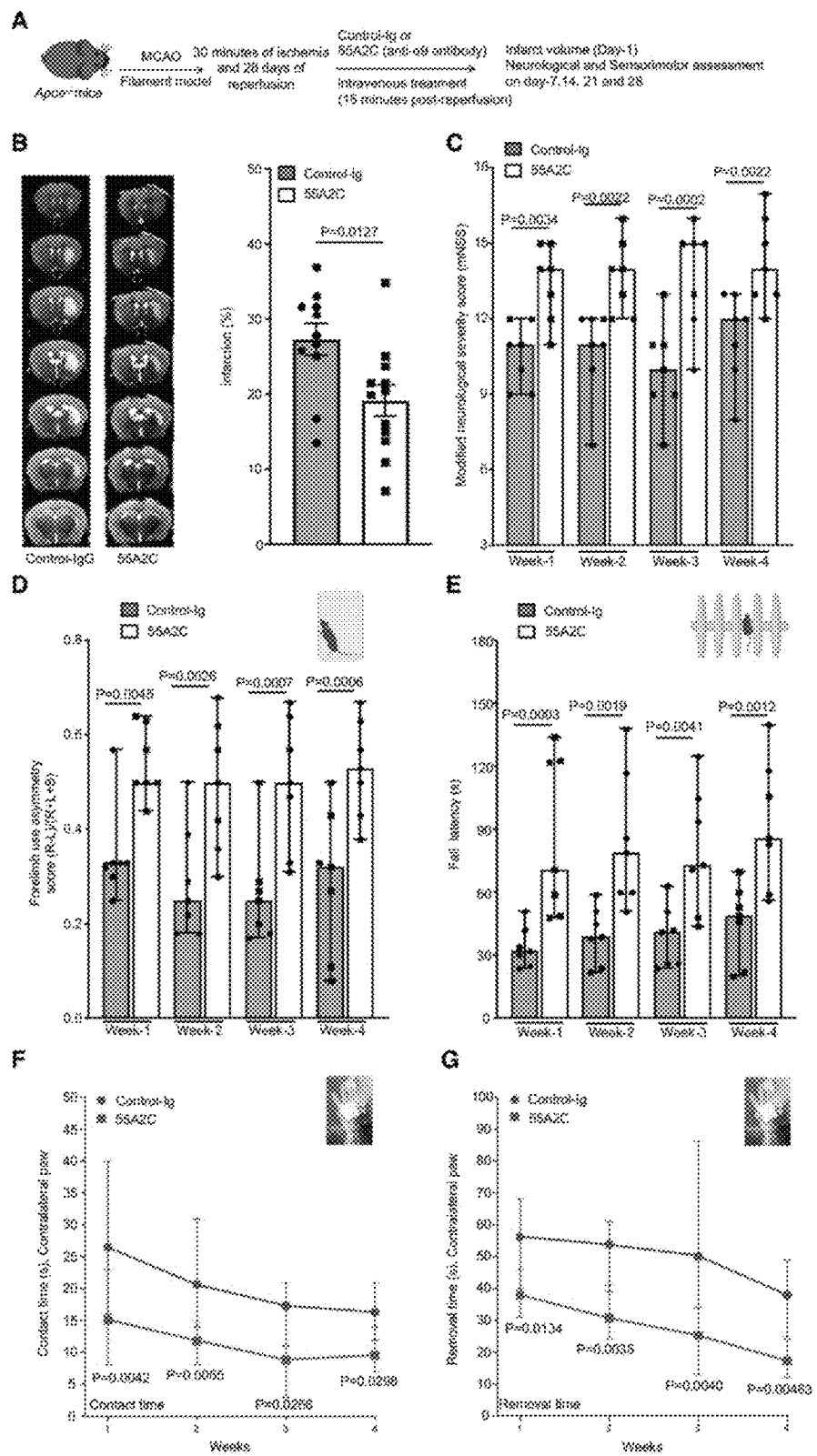
FIGS. 7A-7G: Infusion of anti-integrin α9 antibody improves stroke outcome and enhances long-term sensorimotor activity in the comorbid condition of hyperlipidemia. A. A, Schematic of experimental design. B, Left: Representative magnetic resonance imaging from 1 mouse of each group on day 1. White is the infarct area. Right: Corrected mean infarct volumes of each genotype (n=11 and 12). C, Modified Neurological Severity Score (mNSS) at weeks 1, 2, 3, and 4 based on spontaneous activity, symmetry in the movement of 4 limbs, forepaw outstretching, climbing, body proprioception, and responses to vibrissae touch (higher score indicates a better outcome, n=7/group). Poststroke sensorimotor behavioral recovery at week 1, 2, 3, and 4 as analyzed by D cylinder test, n=7/group, (E) accelerated rotarod, n=7/group, (F) contact time in adhesive tape removal test, n=7/group, and (G) removal time in adhesive tape removal test, n=7/group. Data are mean±SEM (B) and median±range (C-G). Statistical analysis: unpaired t test (B), 2-way ANOVA followed by Fisher LSD multiple comparisons test (C-G). MCAO indicates middle cerebral artery occlusion.

Infusion of Anti-Integrin $\alpha 9$ Antibody Improves Stroke Outcome and Enhances Long-Term Sensorimotor Recovery in a Preexisting Comorbid Condition of Hyperlipidemia We next evaluated the therapeutic potential of targeting integrin $\alpha 9 \beta 1$ using the specific anti-$\alpha 9$ antibody 55A2C. This antibody is a well-characterized integrin $\alpha 9$-blocking antibody that has been shown to have an inhibitory effect on the progression of arthritis and multiple sclerosis in mouse models. (Kanayama M, Kurotaki D, Morimoto J, Asano T, Matsui Y, Nakayama Y, Saito Y, Ito K, Kimura C, Iwasaki N, Suzuki K, Harada T, Li H M, Uehara J, Miyazaki T, Minami A, Kon S and Uede T. Alpha9 integrin and its ligands constitute critical joint microenvironments for development of autoimmune arthritis. *J Immunol.* 2009; 182:8015-25; Ito K, Morimoto J, Kihara A, Matsui Y, Kurotaki D, Kanayama M, Simmons S, Ishii M, Sheppard D, Takaoka A and Uede T. Integrin alpha9 on lymphatic endothelial cells regulates lymphocyte egress. *Proc Natl Acad Sci USA.* 2014; 111:3080-5). Male Apoe$^{-/-}$ mice were randomly assigned to receive either 55A2C or control Ig and susceptibility to ischemia/reperfusion injury was evaluated following 30 minutes of ischemia and up to 4 weeks of reperfusion in the filament model. We decreased the time of ischemia from 60 to 30 minutes in the intervention study because we have observed excessive mortality in Apoe$^{-/-}$ mice at day 7 following 60 minutes of transient ischemia. To mimic clinical conditions of acute stroke therapy, we infused the 55A2C antibody intravenously into male Apoe$^{-/-}$ mice 15 minutes after reperfusion. Apoe$^{-/-}$ mice treated with control Ig served as controls. Infarct volumes were evaluated on day 1, and neurological/sensorimotor tests were performed from 1-week up to 4-weeks (FIG. 7A). Both groups of mice appeared normal during and after treatment. Body-weight and temperature were comparable among treated and control mice (not shown). A significant reduction in infarct volume (~30%) was observed in anti-integrin $\alpha 9$ antibody-treated Apoe$^{-/-}$ mice, compared to control Ig-treated Apoe$^{-/-}$ mice (FIG. 7B). Consistent with this observation, anti-integrin $\alpha 9$ integrin antibody-treated Apoe$^{-/-}$ mice exhibited improved neurological outcome (modified Neuroloigcal Severity Score) from 1 week up to 4 weeks when compared with control Ig-treated mice (FIG. 7C). Importantly, sensorimotor recovery (as analyzed by cylinder test) was improved in the mice treated with the anti-integrin $\alpha 9$ antibody compared to control mice (FIGS. 7D through 7G).

DISCUSSION

While a large number of neuroprotective agents have shown efficacy in preclinical studies, they have been unsuccessful in clinical studies. The lack of success of these neuroprotective agents from bench to bedside is likely due, in part, to the practice of performing preclinical evaluation of mechanisms underlying stroke progression and intervention studies are typically done in healthy male WT animals, whereas human stroke usually occurs during the pathophysiological progression of risk factors such as hyperlipidemia, hypertension, obesity, and influenced by age or biological sex. Therefore, STAIR criterion for preclinical stroke evolution recommends the determination of the associated mechanisms and response to the therapeutic intervention in animal models with the pre-existing comorbidities that adequately mimic the risk factors in human stroke. Herein, we report a novel role of integrin $\alpha 9$ in the pathophysiology of ischemic stroke. Importantly, we have incorporated several STAIR-RIGOR criteria including (1) confirming the findings in two-stroke models: filament and embolic with pre-existing comorbidities such as hyperlipidemia and aging; (2) utilizing male and female mice; (3) predefining inclusion-exclusion criteria; (4) conducting experiments in cohorts and blind fashion, and (5) assessment of infarct volume, short- and long-term functional outcomes on the same mouse. We think that these findings may have a clinical significance for the following reasons: First, we have found that integrin $\alpha 9$ is upregulated on peripheral neutrophils following ischemic stroke and contributes to stable adhesion and transmigration. Second, we provide genetic evidence that irrespective of sex, targeting myeloid-specific integrin $\alpha 9$ improves short- and long-term stroke outcomes in models with pre-existing comorbidities by limiting post-ischemia/reperfusion thrombo-inflammation. Third, as a potential intervention, infusion of specific anti-integrin $\alpha 9$ antibody following reperfusion improves short and long-term stroke outcome that was concomitant with enhanced long-term sensorimotor recovery.

Abrupt reperfusion following the mechanical thrombectomy or r-tPA may promote microvascular dysfunction, oxidative stress and secondary thrombo-inflammation, which further aggravates neuronal death in the ischemic penumbra. Early infiltration of neutrophils is a major hallmark of post-ischemic thrombo-inflammation. Neutrophils can potentiate thrombo-inflammation by several mechanisms including capillary sludging, releasing free radicals, secreting inflammatory mediators and neutrophil extracellular traps. Herein, we report that integrin $\alpha 9$ is up-regulated on peripheral neutrophils for up to six hours of cerebral ischemia/reperfusion injury. Importantly, we demonstrated that genetic deletion of integrin $\alpha 9$ on myeloid cells contribute to stable adhesion and trans-endothelial migration to stimulated brain microvascular endothelial cells. Our results are in agreement with previous in vitro studies that utilized pharmacological approach to demonstrate that integrin $\alpha 9 \beta 1$ is upregulated upon neutrophil activation and contributes to cell adhesion (human umbilical vein endothelial cells) and migration.

We demonstrated that myeloid-specific integrin $\alpha 9^{-/-}$ mice were less susceptible to ischemia/reperfusion injury in the filament and embolic stroke model, suggesting that myeloid-specific integrin $\alpha 9$ contributes to stroke exacerbation. Based on compelling evidence of improved local cerebral blood flow following reperfusion coupled with decreased intracerebral fibrin(ogen) and platelet deposition in myeloid-specific integrin $\alpha 9^{-/-}$ mice, we hypothesized that integrin $\alpha 9$ might exacerbate stroke outcome by potentiating post-ischemia/reperfusion thrombosis. Indeed, myeloid-specific integrin $\alpha 9^{-/-}$ mice on the hyperlipidemic background were less susceptible to experimental arterial thrombosis. Mechanistically, integrin $\alpha 9$ may enhance arterial thrombosis by promoting neutrophil recruitment, neutrophil-mediated platelet aggregation, and neutrophil extracellular traps. Indeed, we found that integrin $\alpha 9$ modulates neutrophil extracellular traps formation. In humans, acute ischemic stroke, the severity of the injury and neurological outcome correlates with a neutrophil influx in the infarcted and peri-infarcted region. Neutrophils promote local inflammation by producing reactive oxygen species, releasing proinflammatory cytokines and chemokines, and by activating canonical NF-κB signaling pathway. We found that myeloid-specific integrin $α9^{-/-}$ mice exhibited reduced neutrophil-influx in the infarcted and peri-infarcted region that was associated with decreased phospho-NFκB expression and inflammatory cytokines TNF-α and IL-1β levels. To define the specific role of neutrophil integrin α9, we generated neutrophil-specific integrin ($α9^{fl/fl}$Mrp8cre$^{+/-}$) mice. We found that neutrophil-specific integrin $α9^{-/-}$ mice exhibited improved stroke outcome at day 1 (not shown). Together, these results suggest that myeloid-specific integrin α9, most likely neutrophil integrin α9, exacerbates stroke outcome by promoting post-ischemia/reperfusion inflammation in addition to thrombosis.

We also investigated the molecular mechanism by which myeloid cell integrin α9 promotes stroke exacerbation. α9β1 is known to bind with multiple ligands, including VCAM-1 (vacular cell adhesion protein 1), VEGF (vascular endothelial growth factor), extracellular matrix proteins including tenascin C, osteopontin, and Fn-EDA that are enriched at the sites of inflammation. Although α9β1 was shown to mediate neutrophil adhesion and transmigration via VCAM, evidence suggests that anti-VCAM-1 antibodies do not protect against FR brain injury. Tenascin C is proinflammatory, and Fn-EDA is both pro-thrombotic and proinflammatory. The role of tenascin C in stroke evolution is not known. We hypothesized that the extracellular matrix protein Fn-EDA, might contribute to α9-mediated stroke exacerbation because of overlapping phenotype in genetic models, which have shown that Fn-EDA is pro-thrombotic and pro-inflammatory and exacerbates stroke and atherosclerosis. Using a BM transplantation approach, we found that Fn-EDA partially contributes to α9-mediated stroke exacerbation, suggesting other ligands including tenascin C or other signaling pathways might also contribute to α9-mediated stroke exacerbation.

Currently, there is no effective intervention to reduce brain damage following reperfusion with tPA or mechanical thrombectomy. Several recent clinical trials utilizing mechanical thrombectomy have provided clear evidence, indicating that partial reperfusion is associated with adverse stroke outcomes. Moreover, many patients treated with rtPA do not show any clinical improvement, despite early recanalization. Among many other reasons, post-ischemia/reperfusion increased cerebral thrombo-inflammation might be one of the reasons for the worse outcome. Therefore, there is an important need for the development of interventions that reduce thrombo-inflammation, following reperfusion. Consequently, we evaluated whether targeting integrin α9 with a specific inhibitor (anti-integrin α9 Ig 55A2C) will improve stroke outcome following reperfusion. We provide evidence that targeting integrin α9 with specific anti-integrin α9 Ig, 55A2C, after reperfusion significantly improved long-term functional outcome (up to 28 days) in stroke model with comorbidity by limiting infarct volume and enhancing long-term sensorimotor recovery. The anti-α9 Ig 55A2C is known to inhibit the binding of α9/NIH cells to the synthetic peptide AEIDGIEL, the sequence similar to the EDGIHEL sequence present in the Fn-EDA segment. We speculate that beneficial effects of the anti-α9 Ig 55A2C on stroke outcome might be partly due to the inhibition of integrin α9 binding to Fn-EDA.

CONCLUSIONS

Our studies unequivocally support the mechanistic role of myeloid-specific integrin α9 in modulating short and long-term stroke outcome by promoting thrombo-inflammation. Targeting myeloid-specific integrin α9 has implications to limit brain damage in stroke patients following reperfusion.

Although the foregoing specification and example fully disclose and enable certain embodiments, they are not intended to limit the scope, which is defined by the claims appended hereto.

All publications, patents and patent applications are incorporated herein by reference. While in the foregoing specification certain embodiments have been described, and many details have been set forth for purposes of illustration, it will be apparent to those skilled in the art that additional embodiments and certain details described herein may be varied considerably without departing from basic principles.

The use of the terms "a" and "an" and "the" and similar referents are to be construed to cover both the singular and the plural, unless otherwise indicated herein or clearly contradicted by context.

The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the technology and does not pose a limitation on the scope of the technology unless otherwise claimed. No language in the specification should be construed as indicating any non-claimed element as essential to the practice of the technology.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the embodiment.

Embodiments are described herein, including the best mode known to the inventors. Variations of those embodiments may become apparent to those of ordinary skill in the art upon reading the foregoing description. The inventors expect skilled artisans to employ such variations as appropriate, and the inventors intend for the embodiments to be practiced otherwise than as specifically described herein. Accordingly, this technology includes all modifications and equivalents of the subject matter recited in the claims appended hereto as permitted by applicable law. Moreover, any combination of the above-described elements in all possible variations thereof is encompassed by embodiments unless otherwise indicated herein or otherwise clearly contradicted by context.

What is claimed is:

1. A method for treating an integrin α9β1-related condition in a mammal, comprising administering an effective amount of an isolated anti-integrin α9 inhibitor to the mammal, wherein the condition is reperfusion injury following stroke, and wherein the inhibitor is fibronectin-EDA (Fn-EDA) peptide SEQ ID NO:1 (CTYSSPEDGIHEC).

2. The method of claim 1, wherein the anti-integrin α9 inhibitor is administered intravenously or intraperitoneally by infusion or injection.

3. The method of claim 1, wherein the anti-integrin α9 inhibitor is administered by local injection.

4. The method of claim 1, further comprising administering at least one additional therapeutic agent to the mammal.

* * * * *

SEQUENCE LISTING

<160> NUMBER OF SEQ ID NOS: 8

<210> SEQ ID NO 1
<211> LENGTH: 13
<212> TYPE: PRT
<213> ORGANISM: Unknown
<220> FEATURE:
<223> OTHER INFORMATION: Description of Unknown:
      Fn-EDA peptide

<400> SEQUENCE: 1

Cys Thr Tyr Ser Ser Pro Glu Asp Gly Ile His Glu Cys
1               5                   10

<210> SEQ ID NO 2
<211> LENGTH: 12
<212> TYPE: PRT
<213> ORGANISM: Unknown
<220> FEATURE:
<223> OTHER INFORMATION: Description of Unknown:
      Tenascin-C peptide

<400> SEQUENCE: 2

Pro Leu Ala Glu Ile Asp Gly Ile Glu Leu Thr Tyr
1               5                   10

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aaaggctgca gctgtcccac atggacgaag                                        30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tttagagaga tattcttcac agcccccaaa                                        30

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
accacagtcc atgccatcac                                                   20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
tccaccaccc tgttgctgta                                              20

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Glu Ile Asp Gly Ile Glu Leu
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Asp Gly Ile His Glu Leu
1               5
```